United States Patent [19]

Stern et al.

[11] Patent Number: 5,712,096
[45] Date of Patent: Jan. 27, 1998

[54] OLIGORIBONUCLEOTIDE ASSAYS FOR NOVEL ANTIBIOTICS

[75] Inventors: Seth Stern, Sterling; Prakash Purohit, Worcester, both of Mass.

[73] Assignee: University of Massachusetts Medical Center, Worcester, Mass.

[21] Appl. No.: 498,402

[22] Filed: Jul. 5, 1995

Related U.S. Application Data

[63] Continuation-in-part of Ser. No. 294,450, Aug. 23, 1994, abandoned.

[51] Int. Cl.[6] .............................. C12Q 1/68; C07H 21/02; C12P 19/34
[52] U.S. Cl. .............................. 435/6; 536/23.1; 435/91.3
[58] Field of Search ...................... 435/6, 91.3; 536/23.1

[56] References Cited

U.S. PATENT DOCUMENTS

| | | |
|---|---|---|
| 4,330,621 | 5/1982 | Davies et al. . |
| 5,223,618 | 6/1993 | Cook et al. . |
| 5,270,170 | 12/1993 | Schatz et al. . |

FOREIGN PATENT DOCUMENTS

| | | |
|---|---|---|
| WO 81/01419 | 5/1981 | WIPO . |
| WO 93/23532 | 11/1993 | WIPO . |

OTHER PUBLICATIONS

PCT Search Report US 95/10721.
C. Bonny et al., "Analysis of streptomycin–resistance of *Escherichia coli* mutants", *Biochimica et Biophysica Acta*, 1089:213–219, (1991).
E.A. De Stasio et al., "Effects of Mutagenesis of a Conserved Base–paired Site near the Decoding Region of *Escherichia coli* 16 S Ribosomal RNA", *J. Mol. Biol.*, 212:127–133, (1990).
M. Gravel et al., "Cross–Linking of Streptomycin to the 16S Ribosomal RNA of *Escherichia coli*", *Biochemistry*, 26:6227–6232, (1987).
D. Leclerc et al., "A conformational switch involving the 915 region of *Escherichia coli* 16 S ribosomal RNA", *FEBS Letters*, 279:171–174, (1991).
R. Schroeder, "Dissecting RNA function", *Nature*, 370:597–598, (1994).
U. von Ahsen et al., "Antibiotic inhibition of group I ribozyme function", *Nature*, 353:368–370, (1991).
Dahlberg, A.E., "The Functional Role of Ribosomal RNA in Protein Synthesis", 1989, *Cell*, 57:525–29.
De Stasio, E.A., et al., "Mutations in 16S Ribosomal RNA Disrupt Antibiotic—RNA Interactions", 1989, *The EMBO J.*, 8(4):1213–16.
Green, M.R., "Molecular Mechanisms of Tat and Rev", 1993, *AIDS Res. Rev.*, 3:41–55.
Hooper, I.R., "The Naturally Occurring Aminoglycoside Antibiotics", 1982, *Aminoglycoside Antibiotics*, Ch. 1, pp. 1–266.
Moazed, D., et al., "Interaction of Antibiotics with Functional Sites in 16S Ribosomal RNA", 1987, *Nature*, 327:389–94.

(List continued on next page.)

*Primary Examiner*—W. Gary Jones
*Assistant Examiner*—Amy Atzel
*Attorney, Agent, or Firm*—Fish & Richardson P.C.

[57] ABSTRACT

The oligoribonucleotide analogs of the invention are relatively small, three-dimensional structures derived from larger parental RNA molecules. The analogs include a first nucleic acid structure including one or more nucleotide sequences that are derived from a region of parental RNA, wherein in its native state, the region binds to a ligand, e.g., an aminoglycoside, with a parental RNA ligand binding pattern, and a second nucleic acid structure including one or more nucleotide sequences combined with the first nucleic acid structure to form the analog and provide the analog with a conformation that binds the ligand with a ligand binding pattern that is substantially identical to the parental RNA ligand binding pattern. These analogs can be used to identify novel therapeutic compounds.

31 Claims, 9 Drawing Sheets

OTHER PUBLICATIONS

Moazed, D., et al., "Transfer RNA Shields Specific Nucleotides in 16S Ribosomal RNA from Attack by Chemical Probes", 1986, *Cell*, 47:985–94.

Needels, M.C., et al., "Generation and Screening of an Oligonucleotide–Encoded Synthetic Peptide Library", 1993, *Proc. Natl. Acad. Sci. USA*, 90:10700–704.

Noller, H.F., "Ribosomal RNA and Translation", 1991, *Annu. Rev. Biochem.*, 60:191–227.

Noller, H.F., et al., "Unusual Resistance of Peptidyl Transferase to Protein Extraction Procedures", 1992, *Science*, 256:1416–19.

Noller, H.F., "Structure of Ribosomal RNA", 1984, *Ann. Rev. Biochem.*, 53:119–62.

Peattie, D.A., "Chemical Probes for Higher–Order Structure in RNA", 1980, *Proc. Natl. Acad. Sci. USA*, 77(8):4679–82.

Purohit, et al., "Interactions of a Small RNA with Antibiotic and RNA Ligands of the 30S Subunit", *Nature*, 370:659–662, (1994).

Rosen, C., et al., "Tat and Rev: Positive Regulators of HIV Gene Expression", 1990, *AIDS*, 4(6):499–509.

Stern, S., et al., "Structural Analysis of RNA Using Chemical and Enzymatic Probing Monitored by Primer Extension", 1988, *Methods in Enzymology*, 164(33):481–89.

Thompson, J., et al., "The Binding of Thiostrepton to 23S Ribosomal RNA", 1991, *Biochemie*, 73:1131–35.

Woodcock, J., et al., "Interaction of Antibiotics with A–and P–Site–Specific Bases in 16S Ribosomal RNA", 1991, *The EMBO J.*, 10(10):3099–103.

Zapp, M.L., et al., "Small Molecules that Selectively Block RNA Binding of HIV–1 Rev Protein Inhibit Rev Function and Viral Production", 1993, *Cell*, 74:969–78.

Gu et al., "Anti–peptidyl transferase leader peptides of attenuation–regulated chloramphenicol–resistance genes", *Proc. Natl. Acad. Sci.*, 91:5612–5616, (1994).

Copy of Written Opinion mailed Oct. 16, 1996 for PCT/US95/10721.

Draper et al. (1995) *J. Mol. Biol.* 249:231–8.

Brink et al. (1994) *Nucl. Acids Res.* 22:325–31.

Douthwaite (1992) *Nucl. Acids Res.* 20:4717–20.

Krueger et al. (1996) *J. Antibiot.* 39:1298–303.

Dahlberg et al. (1978) *Antimicrob. Agents Chemother.* 13:331–9.

Wang et al. (1993) *Biochemistry* 32:12279–82.

Puglisi et al. (1993) *Proc. Natl. Acad. Sci. USA* 90:3680–84.

Von Ashen and Noller (1993) *Science* 260:1500–3.

Ryan et al. (1991) *J. Mol. Biol.* 221:1257–68.

Turner et al. (1988) *Ann. Rev. Biophys. Biophys. Chem.* 17:167–92.

Wittman–Liebold et al. (1995) *Biochem. Cell Biol.* 73:1187–97.

Lu and Draper (1995) *Nucleic Acids Res.* 23:3426–33.

Xing and Draper (1996) *Biochemistry* 35:1581–88.

Limbird, Lee E. *Cell Surface Receptors: A Short Course on Theory and Methods* (1986) Martinus Nijhoff Publishing, Boston, pp. 82–88.

Burt, David R. "Receptor Binding Methodology and Analysis" in *Receptor Binding in Drug Research*, ed. Robert A. O'Brien (1986) Marcel Dekker, Inc., NY, NY.

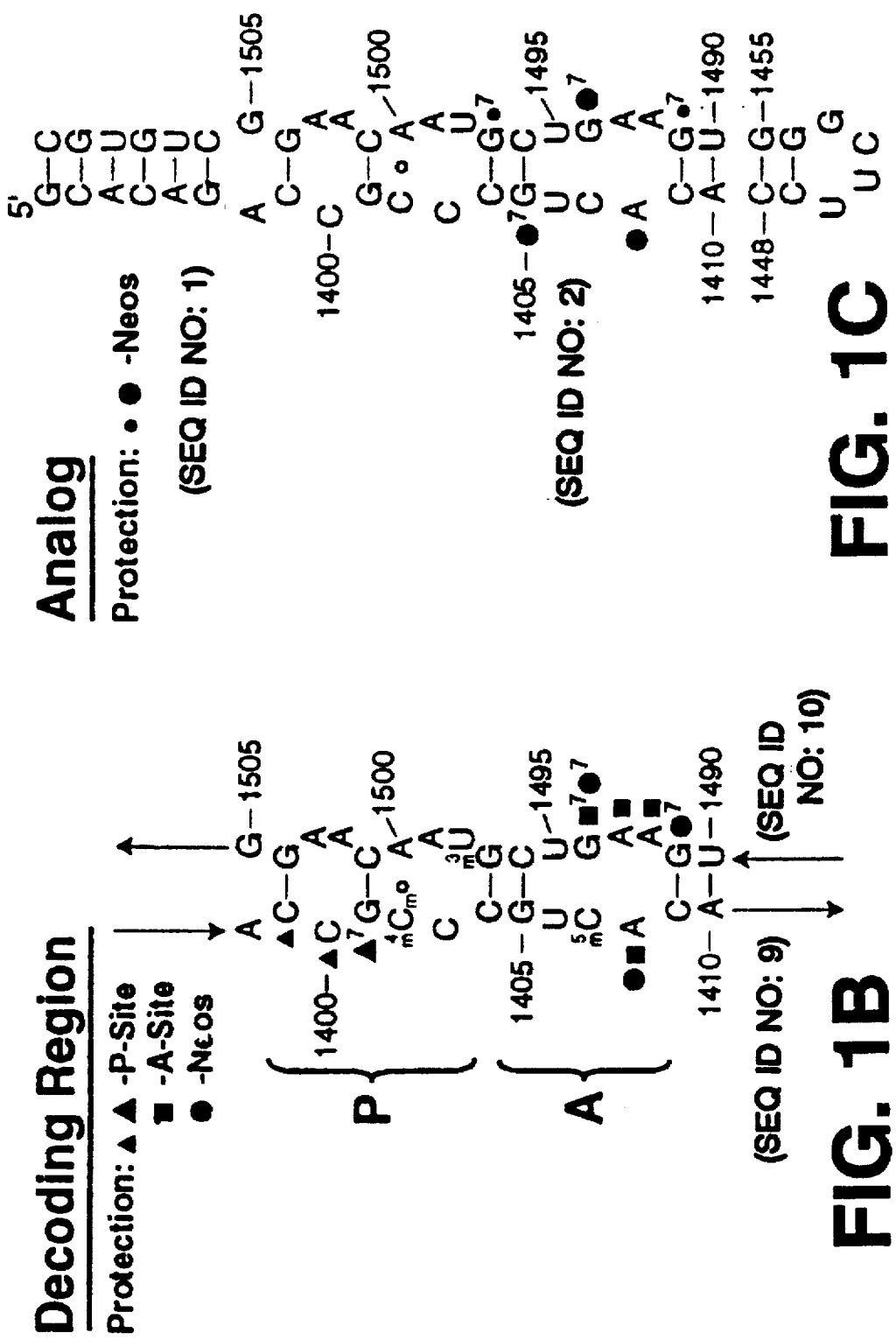

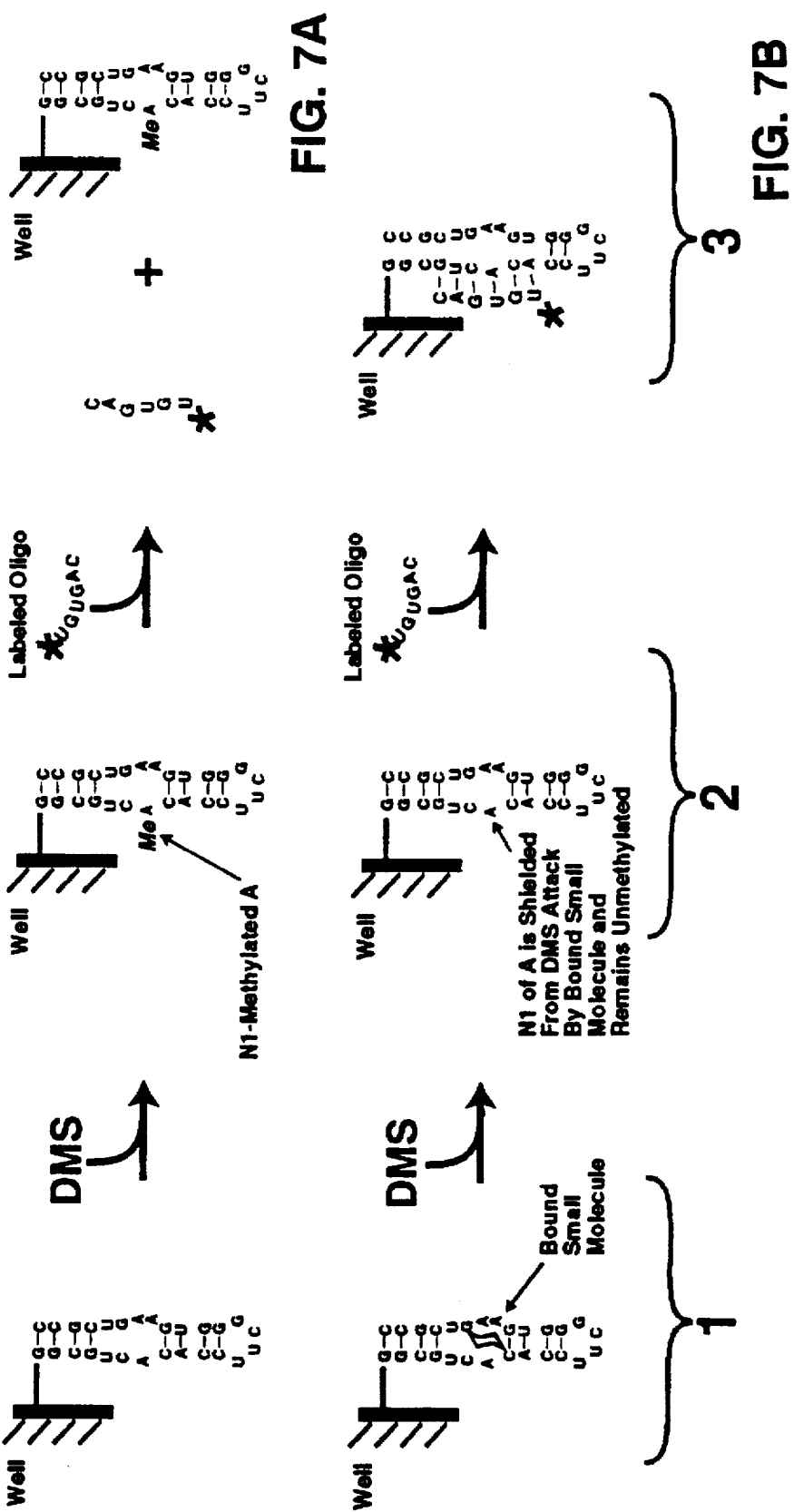

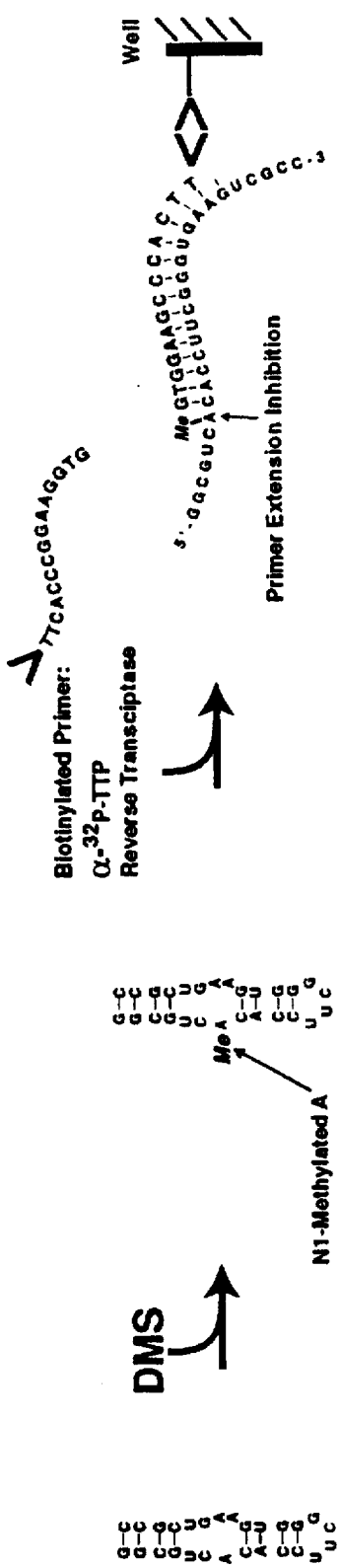
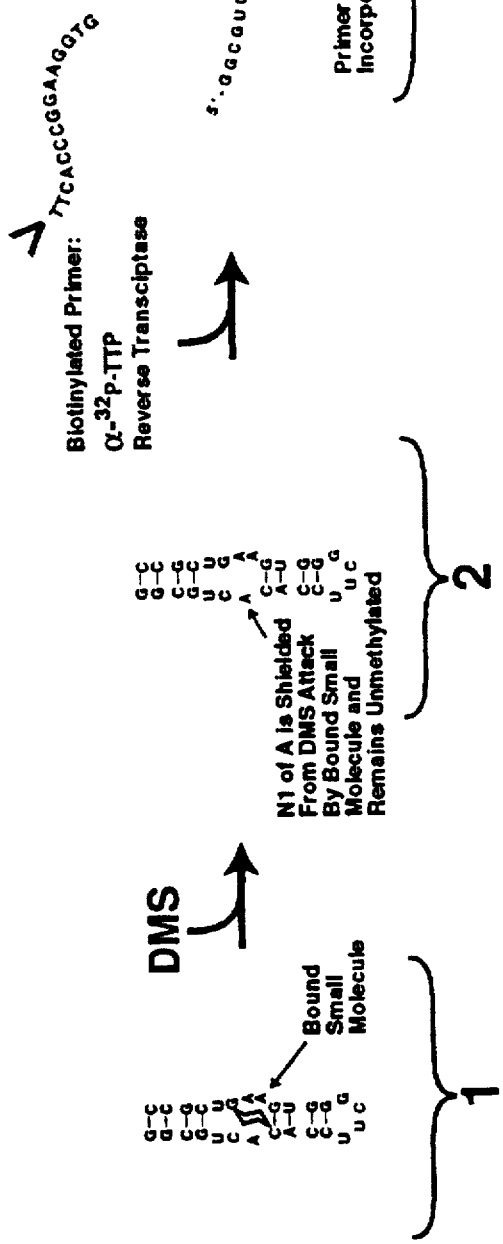
FIG. 8A
FIG. 8B

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( x i ) SEQUENCE DESCRIPTION: SEQ ID NO: 1:

GCACAGACCG CCCGUCACAC CUUCGGGUGA AGUCGUAACA AGGCUGUGC    49

( 2 ) INFORMATION FOR SEQ ID NO: 2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CGUCACACCU UCGGGUGAAG UCG    23

( 2 ) INFORMATION FOR SEQ ID NO: 3:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( x i ) SEQUENCE DESCRIPTION: SEQ ID NO: 3:

GGGGAUUGAA AAUCCCC    17

( 2 ) INFORMATION FOR SEQ ID NO: 4:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GGUCAUCUUG GGGUGAUGAC C    21

( 2 ) INFORMATION FOR SEQ ID NO: 5:

( i ) SEQUENCE CHARACTERISTICS:
        ( A ) LENGTH: 17
        ( B ) TYPE: nucleic acid ( C ) STRANDEDNESS: single
( D ) TOPOLOGY: linear ( x i ) SEQUENCE DESCRIPTION: SEQ ID NO: 5:

GGGAGCGUCA UCACAUA                                                                                                          17

( 2 ) INFORMATION FOR SEQ ID NO: 6:

( i ) SEQUENCE CHARACTERISTICS:
( A ) LENGTH: 14
( B ) TYPE: nucleic acid
( C ) STRANDEDNESS: single
( D ) TOPOLOGY: linear ( x i ) SEQUENCE DESCRIPTION: SEQ ID NO: 6:

GGGACUUCGG UCCC                                                                                                              14

( 2 ) INFORMATION FOR SEQ ID NO: 7:

( i ) SEQUENCE CHARACTERISTICS:
( A ) LENGTH: 13
( B ) TYPE: nucleic acid
( C ) STRANDEDNESS: single
( D ) TOPOLOGY: linear ( x i ) SEQUENCE DESCRIPTION: SEQ ID NO: 7:

GGCGCUUUGC GCC                                                                                                               13

( 2 ) INFORMATION FOR SEQ ID NO: 8:

( i ) SEQUENCE CHARACTERISTICS:
( A ) LENGTH: 66
( B ) TYPE: nucleic acid
( C ) STRANDEDNESS: single
( D ) TOPOLOGY: linear ( x i ) SEQUENCE DESCRIPTION: SEQ ID NO: 8:

GCACUAUGGG CGCAGCGUCA AUGACGCUGA CGGUACAGGC CAGACAAUUA UUGUCUGGUA                    60

UAGUGC                                                                                                                       66

( 2 ) INFORMATION FOR SEQ ID NO: 9:

( i ) SEQUENCE CHARACTERISTICS:
( A ) LENGTH: 13
( B ) TYPE: nucleic acid
( C ) STRANDEDNESS: single
( D ) TOPOLOGY: linear ( x i ) SEQUENCE DESCRIPTION: SEQ ID NO: 9:

ACCGCCCGUC ACA                                                                                                               13

( 2 ) INFORMATION FOR SEQ ID NO: 10:

( i ) SEQUENCE CHARACTERISTICS:
( A ) LENGTH: 16
( B ) TYPE: nucleic acid
( C ) STRANDEDNESS: single
( D ) TOPOLOGY: linear ( x i ) SEQUENCE DESCRIPTION: SEQ ID NO: 10:

UGAAGUCGUA ACAAGG                                                                                                            16

( 2 ) INFORMATION FOR SEQ ID NO: 11:

( i ) SEQUENCE CHARACTERISTICS:
( A ) LENGTH: 27
( B ) TYPE: nucleic acid

```
            ( C ) STRANDEDNESS: single
            ( D ) TOPOLOGY: linear ( x i ) SEQUENCE DESCRIPTION: SEQ ID NO: 11:

GGCGUCACAC CUUCGGGUGA AGUCGCC                                              27

( 2 ) INFORMATION FOR SEQ ID NO: 12:

( i ) SEQUENCE CHARACTERISTICS:
            ( A ) LENGTH: 13
            ( B ) TYPE: nucleic acid
            ( C ) STRANDEDNESS: single
            ( D ) TOPOLOGY: linear ( x i ) SEQUENCE DESCRIPTION: SEQ ID NO: 12:

ACCGCCCGUC ACA                                                              13

( 2 ) INFORMATION FOR SEQ ID NO: 13:

( i ) SEQUENCE CHARACTERISTICS:
            ( A ) LENGTH: 16
            ( B ) TYPE: nucleic acid
            ( C ) STRANDEDNESS: single
            ( D ) TOPOLOGY: linear ( x i ) SEQUENCE DESCRIPTION: SEQ ID NO: 13:

UGAAGUCGUA ACAAGG                                                           16

( 2 ) INFORMATION FOR SEQ ID NO: 14:

( i ) SEQUENCE CHARACTERISTICS:
            ( A ) LENGTH: 15
            ( B ) TYPE: nucleic acid
            ( C ) STRANDEDNESS: single
            ( D ) TOPOLOGY: linear ( x i ) SEQUENCE DESCRIPTION: SEQ ID NO: 14:

TTCACCGGA AGGTG                                                             15
```

OLIGORIBONUCLEOTIDE ASSAYS FOR NOVEL ANTIBIOTICS

This application is a continuation-in-part application of U.S. Ser. No. 08/294,450, filed Aug. 23, 1994 now abandoned.

STATEMENT AS TO FEDERALLY SPONSORED RESEARCH

This invention was made with Government support under NIH grant RO1-GM48536. The Government has certain rights in the invention.

BACKGROUND OF THE INVENTION

The field of the invention is the evaluation of ribonucleic acid (RNA)-interacting therapeutics, for example, antibiotics that bind to 16S rRNA and inhibit protein synthesis.

Ribosomes are large, multisubunit ribonucleoproteins (RNPs) responsible for protein synthesis, and are highly conserved across phyla, both structurally and functionally. They include large (50S) and small (30S) subunits assembled from ribosomal RNAs (rRNAs) and proteins bound to the rRNA. The 30S ribosomal subunit contains 16S rRNA, while the 50S subunit contains 23S rRNA. Ribosomes synthesize proteins when correctly bound to messenger RNA (mRNA) and transfer RNA (tRNA).

The proper assembly of the various components involved in protein synthesis is thought to be directed by binding sites on the rRNAs. Two binding sites of importance on the rRNA for protein synthesis are the so-called A and P sites, which accommodate the incoming aminoacyl-tRNA (A site) and the peptidyl-tRNA (P site), respectively. In prokaryotes, these sites are composed in part of highly ordered structures of the 16S rRNA, probably in the cleft of the 30S subunit.

Ribosomes are structurally similar in all species (including eukaryotes), although the primary nucleotide sequences of rRNA molecules differ. For a review of ribosomal RNA function, see Noller *In The RNA World*, Gesteland and Atkins (eds.), 137–84 (CSHL Press, New York, 1993); Noller et al., *In The Ribosome: Structure, Function, and Evolution*, Hill, et al. (eds.), 73–92 (American Soc. for Microbiol., Washington, D.C., 1990).

It is now generally accepted that 16S and 23S rRNAs (found in the 50S ribosomal subunit; analogous eukaryotic rRNAs are 28S, 5.8S, and 5S rRNA in the 60S ribosomal subunit, and 18S rRNA in the 40S ribosomal subunit) play important, if not critical, roles in the decoding and peptidyl transferase activities of ribosomes (Noller et al., 1990, supra, Noller, supra).

Most antibiotics that inhibit protein synthesis act directly on ribosomes. For example, some mutations in ribosomal proteins can result in antibiotic resistance (Birge and Kurland (1969) *Science*, 166:1282; Ozaki et al. (1969) *Nature*, 222:333; Davies et al. (1965) *Science*, 149:1096). Work in this field has also demonstrated that aminoglycoside antibiotics interact with sites on ribosomal subunits, resulting in protection of RNA as visualized by RNA footprint assays (e.g., Moazed and Noller (1987) *Nature*, 327:389; Woodcock et al. (1991) *EMBO J.*, 10:3099; Thompson and Cundliffe (1991) *Biochimie*, 73:1131–1135).

Such research has shown that specific nucleotides in 16S rRNA are the binding targets of aminoglycosides such as neomycin, streptomycin, hygromycin, gentamycin, and tetracycline. Similarly, specific nucleotides in 23S rRNA are targeted by numerous MLS compounds (macrolides, lincomycins, and streptogramins), including erythromycin.

Some antibiotics (e.g., edeine, pactamycin, apramycin, and neamine) inhibit protein synthesis by interfering with binding between tRNA and the A- or P-sites on the ribosome during translation (Woodcock et al. (1991) *EMBO J.*, 10:3099). Interactions of many of these compounds with 16S rRNA in the 30S ribosomal subunit have been mapped to various functional sites, primarily by chemical footprinting assays. Other antibiotic compounds, such as the peptide antibiotic, thiostrepton, have been shown to similarly interact with 23S rRNA in 50S subunits (Thompson and Cundliffe (1991) supra).

Several factors, all related to the structural complexity of the ribosome, complicate screening assays that rely on binding of a potential drug candidate to a ribosomal target. First, obtaining large quantities of purified ribosomes, even from common bacteria, is difficult. Second, ribosomes often degrade under typical screening conditions. Third, it is unclear to what degree a compound's ability to bind to ribosomes or RNA molecules is indicative of its antibiotic potential.

In particular, even small, well-defined RNA molecules are complex targets for such drug screening assays, because they support multiple binding sites for small molecules. For example, the polyanionic phosphodiester backbone of a nucleic acid presents an attractive binding target for many compounds carrying a positive charge, as does the hydrophobic helical core for many aromatic compounds. Thus, compounds that bind to nucleic acids moieties not directly related to the targeted function are less likely to be useful drugs.

SUMMARY OF THE INVENTION

The present invention is based on the discovery that relatively small RNA molecules, "oligoribonucleotide analogs," that are derived from portions of larger parental RNA structures (e.g., RNPs), surprisingly retain important parental structure even without the rest of the parental RNA sequence(s) and associated proteins. Oligoribonucleotide analogs are useful in new methods of screening candidate compounds for antibiotic activity.

Accordingly, in one aspect, the invention features an oligoribonucleotide analog of a region of a parental ribonucleic acid (RNA) including (i) a first nucleic acid structure having one or more nucleotide sequences, the first structure being derived from the region of parental RNA, e.g., 16S ribosomal RNA (rRNA), wherein in its native state, the region binds to a ligand with a parental RNA ligand binding pattern, and (ii) a second nucleic acid structure having one or more nucleotide sequences combined with the first nucleic acid structure to form the analog and provide the analog with a conformation that binds the ligand with a ligand binding pattern that is substantially identical to the parental RNA ligand binding pattern.

As used herein, the terms "oligoribonucleotide analog" or "analog" mean a single-stranded molecule composed of ribonucleic acids that is smaller than the parental RNA (e.g., having a total of approximately 10 to several hundred nucleotides) that folds into a discreet three-dimensional conformation that mimics the structure of a subdomain of a larger parental RNA molecule. However, modified RNAs, e.g., phosphorothioates, deoxynucleotides, or 2'-O-methyl substitutions, can also be used to confer stability to the analogs.

The oligoribonucleotide analogs are produced in vitro either by transcription of DNA templates with RNA polymerase, e.g., T7 RNA polymerase, or by chemical synthesis with a commercially available DNA/RNA synthesizer. Generally, there are from approximately 10 nucleotides up to several hundred nucleotides (and preferably 20 to 50 nucleotides) in an oligoribonucleotide analog that are identical to nucleotides in a region of parental RNA (the number of parentally derived nucleotides is determined by the sequence necessary to mimic a functional subdomain).

The second nucleic acid structure can contain heterologous (artificial) nucleotide sequences, i.e., sequences that do not exist in the parental RNA, that, when combined with the first nucleic acid structure, stabilize the structure of the analog. As used herein, the term "combined" means that the nucleotide sequences of the first and second nucleic acid structures are linked, e.g., by covalent and non-covalent bonds (e.g., hydrogen bonds, ionic (electrostatic) interactions, and/or van der Walls forces), in such a way that the complete analog has a ligand binding pattern that is substantially identical to the ligand binding pattern of the parental RNA in the native state, e.g., in the intact ribosome.

As used herein, the term "parental RNA" molecule or structure refers to the naturally occurring (or "native"), intact RNA molecule or structure (including associated proteins and other components of the structure) from which the first nucleic acid structure of the oligoribonucleotide is derived. The parental RNA can be ribosomal RNA, viral RNA such as HIV RNA, messenger RNA, or specific cellular RNA regulatory elements. Preferred HIV RNA oligoribonucleotide analogs are derived from the Tat binding site (TAR) or the Rev Response Element (RRE), more preferably from a portion of the RRE having the sequence GCACUAUGGGCGCAGCGU-CAAUGACGCUGACGGUACAGGCCAGA-CAAUUAUUGUCUGGUAUAGUGC (SEQ ID NO:8). Further, if the parental RNA-binding "ligand" is an aminoglycoside, such as neomycin, the rRNA binding pattern can also be referred to as the "aminoglycoside protection profile" of the parental RNA.

In specific embodiments, the region of parental RNA is a decoding region of 16S rRNA, e.g., including nucleotides 1398–1410 and 1490–1505 of 16S rRNA (of *Escherichia coli*). In other embodiments, the region is the A site subdomain of the decoding region of 16S rRNA, e.g., including nucleotides 1404–1410 and 1490–1497 of 16S rRNA (of *E. coli*). The "decoding region" is the portion of the 16S rRNA which, in the intact ribosome, accurately aligns tRNA with mRNA for correct codon-anticodon base pairing during protein synthesis. The decoding region consists of the "A site," which in the intact ribosome accommodates the incoming aminoacyl-tRNA, and the "P site," which contains the peptidyl-tRNA complex (the tRNA still linked to all the amino acids added to the chain thus far). Other possible rRNAs which can be used in the invention are 23S rRNAs of prokaryotes; or 28S, 5.8S, 5S and 18S rRNAs of eukaryotes.

The second nucleic acid structure of the analog can include a stable stem loop such as tetraloop, e.g., having the nucleotide sequence 5'-CCUUCGGG-3', in which the nucleotides UUCG form the loop, and the nucleotides CC and GG are paired. The second nucleic acid structure can also include two nucleotide sequences forming a based-paired stable helix, also known as a "nucleotide clamp." For example, such a clamp can have the nucleotide sequence:

3'-CGUGUC-5'   or   3'-CC-5'
5'-GCACAG-3'        5'-GG-3'.

Specific analogs of the invention include a first nucleic acid structure derived from a decoding region of 16S rRNA, and a second nucleic acid structure including a tetraloop and a base-paired nucleotide clamp. For example, the decoding region can include nucleotides 1398–1410 and 1490–1505 of 16S rRNA, the tetraloop can have nucleotide sequence 5'-CCUUCGGG-3', the base-paired nucleotide clamp can have the nucleotide sequence:

3'-CGUGUC-5'

5'-GCACAG-3', and the complete linear nucleotide sequence of the combined first and second nucleotide structures of the analog would be 5'-GCACAGACCGCCCGUCACACCUUCGG-GUGAAGUCGUAACAAGGCUGUGC-3' (SEQ ID NO:1).

In another embodiment, the analog can be derived from a decoding region including nucleotides 1404–1410 and 1490–1497 of 16S rRNA, the tetraloop can have nucleotide sequence 5'-CCUUCGGG-3', the base-paired nucleotide clamp can have the nucleotide sequence:

3'-CC-5'

5'-GG-3', and the complete linear nucleotide sequence of the combined first and second nucleotide structures of the analog would be 5'-GGCGUCACACCUUCGGGUGAAGUCGCC-3' (SEQ ID NO:11).

In another aspect, the invention features an affinity assay for determining the potential antibiotic or therapeutic activity of a test compound, the assay including the steps of (i) mixing a test compound with an oligoribonucleotide analog of the invention under conditions that allow formation of a binding complex between the analog and the test compound, and (ii) detecting the formation of a binding complex, wherein the presence of a binding complex indicates that the test compound has potential antibiotic activity.

It is preferred that the test compound show specific affinity, i.e., that its particular interaction with the oligoribonucleotide analog is highly repeatable and affects the same nucleotide(s) in the analog. The higher the affinity of the test molecule for the oligoribonucleotide, the higher its potential usefulness as an therapeutic/antibiotic compound.

In specific embodiments, the analog is labelled, e.g., with a fluorescent or radioactive label, and immobilized on a surface, and the binding complex is detected by monitoring changes in the signal of the label when a test compound is bound to the analog, or the analog is immobilized on a surface, the test compound is labelled, and the binding complex is detected by detecting any of the label bound to the surface via the analog.

In a preferred embodiment, the affinity assay is used to identify potentially useful compounds from a mixture of compounds. It includes the steps of contacting the analog with numerous test compounds existing in a mixture, isolating the analog-test compound complexes, and determining the identity of the test compounds that bind with the analog. One example of such a mixture of compounds is an encoded library of small molecules (see, e.g., Needels et al. (1993) *PNAS* 90:10700–04).

In an encoded library, the molecular structure of synthetic small molecules, e.g., peptides or other organic molecules, are encoded, e.g., by a DNA strand. For example, in an encoded peptide library, the specific DNA sequences for each peptide are attached to beads (with a unique sequence encoding the peptide sequence attached to each bead), as are the small peptide molecules encoded by the DNA sequences. If one or more of these test molecules shows an affinity for the labelled oligoribonucleotide analog of the invention, it can be isolated, e.g., by biotinylation/streptavidin interaction or flucrescently activated cell sorting of labelled molecules, and identified by standard means, e.g., polymerase chain reaction (PCR) or dideoxy sequencing.

The invention also features a competitive binding assay for determining the potential antibiotic or therapeutic activity of a test compound, the assay including the steps of (i) mixing an analog with an analog-binding ligand under conditions that allow formation of a first binding complex between the analog and the ligand, (ii) mixing a test compound with the first binding complex under conditions that allow the test compound to disrupt the first binding complex to form a second binding complex between the analog and the test compound, and (iii) detecting the disruption of the first binding complex, wherein the disruption of the first binding complex indicates that the test compound has potential antibiotic activity.

In specific embodiments, the ligand is labelled, e.g., fluorescently or radioactively, the analog is immobilized on a surface, and the disruption of the first binding complex is detected by monitoring any decrease in the signal of the label when a test compound displaces the ligand from the first binding complex. Alternatively, the analog can be labelled, the ligand immobilized on a surface, and the disruption of the first binding complex detected by monitoring any decrease in the signal of the label when a test compound displaces the analog from the first binding complex.

In a preferred embodiment, the ligand is an aminoglycoside, and is immobilized, e.g., covalently cross-linked, to a solid support, e.g., a nylon or cellulose-derived membrane, microtiter plate, or other plastic support, and then incubated with a labelled (fluorescently tagged or radiolabeled) oligoribonucleotide analog. The aminoglycoside-analog complexes are then challenged competitively with test compounds, or mixtures of compounds, cell extracts, etc., and those compounds that can effectively bind to the analog will displace the analog from the aminoglycoside-analog complex. Other embodiments include cross-linking the analog to a solid support and challenging with a mixture of the aminoglycoside and test compounds.

In another aspect, the invention features an in situ footprinting assay for determining the potential antibiotic or therapeutic activity of a test compound, the assay including the steps of (i) mixing an oligoribonucleotide analog with a test compound under conditions that allow formation of a binding complex between the analog and the test compound, (ii) incubating the binding complex with a chemical probing reagent and monitoring for an effect of the reagent on the analog in the complex, (iii) in a separate control reaction, incubating the analog unbound to any test compound with the chemical probing reagent and monitoring for an effect of the reagent on the unbound analog, and (iv) comparing any effects of the probing reagent on the analog in the binding complex and on the unbound analog, wherein prevention of an effect of the reagent on the analog in the binding complex caused by the reagent on the unbound analog indicates that the test compound has potential antibiotic activity.

In specific embodiments, the chemical probing reagent is dimethyl sulfate (DMS), kethoxal (KE), or carbodiimmide, e.g., 1-cyclohexyl-3-(2-morpholinoethyl)carbodiimide metho-p-toluene sulfonate (CMCT). These and other probing reagents covalently modify, e.g., methylate in the case of DMA, a nucleotide in the analog when unbound to any test compound. The effect of the probing reagent can be monitored by use of a labelled oligonucleotide, e.g., having the sequence CAGUGU, that is complementary to a portion of the analog, and thus hybridizes to the analog when the analog is protected by the test compound from modification, and does not hybridize to the analog when modified, e.g., methylated by the reagent, the presence of the label after completion of the assay indicating that the test compound has potential antibiotic activity. Alternatively, the effect of the probing reagent is monitored by use of an oligonucleotide primer, e.g., having the sequence TTCACCCGGAAG-GTG (SEQ ID NO:12), that is complementary to a portion of the analog, a labelled nucleotide, and reverse transcriptase, wherein extension of the primer on the analog with the labelled nucleotide does not occur when the analog is methylated by the reagent, the presence of the label after completion of the assay indicating that the test compound has potential antibiotic or therapeutic activity.

Other potential therapeutics or antibiotics that can be identified include human immunodeficiency virus (HIV) therapeutics (e.g., molecules that inhibit viral replication or protein synthesis). Regions of interest include those involved in viral replication (e.g., Tat binding site (TAR) and the Rev Response Element (RRE) of RNA).

As used herein, "protection," e.g., by an aminoglycoside or thiostrepton, refers to the characteristic footprint or "profile," i.e., a pattern of bands on a polyacrylamide gel which results following various chemical treatments (e.g., dimethyl sulfate, kethoxal, 1-cyclohexyl-3-(3-morpholinoethyl)-carbodiimide metho-p-toluene sulfonate) of RNA previously exposed to the protective molecule. These footprint assays are routine, using methods well known in the art (see, for example Moazed et al., 1986, *Cell*, 47:985–94; Stern et al., (1988) *Meth. Enzymol.* 164:481–489; Peattie and Gilbert (1980) *PNAS* 77:4679–82).

A major advantage of the methods described herein is that these methods allow the discovery of new antibiotic compounds or molecules without the labor and expense of standard antimicrobial activity assays. By using the oligoribonucleotide analogs that mimic the aminoglycoside interacting site (ligand binding site) of a parent RNA, compounds which are likely to have antibiotic, protein synthesis-inhibiting, or viral-inhibiting properties can be quickly and inexpensively identified, even if very large-scale screening protocols are used with hundreds of test molecules. The assays are amenable to automation, which increases ease of large-scale screening methods.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DESCRIPTION OF THE DRAWINGS

FIGS. 1A–1E are schematic depictions of 16S rRNA, the decoding region, two oligoribonucleotide analog, and probing data. FIG. 1A is a schematic diagram of 16S rRNA showing nucleotides outside the decoding region (boxed) implicated in tRNA-30S subunit interactions at the A- and P-sites (Noller et al., *In The Ribosome: Structure, Function, and Evolution* (Eds. Hill, Dahlberg, et al.) American Soc. for Microbiol., Washington, D.C., 1990, pp. 73–92; Moazed et al., 1986, *Cell*, 47:985–94, Moazed et al., 1990, *J. Mol. Biol.*, 211:135–45). The position of a zero length cross-link between the tRNA anticodon loop and C1400 (cytosine at location 1400) in the decoding region (AC XL) is indicated (Prince et al., 1982, *Proc. Natl. Acad. Sci. USA*, 79:5450–54). FIG. 1B shows the decoding region (SEQ ID NOS:9 and 10) and the nucleotides protected from DMS modification (at N1 of A, N3 of C, and N7 of G) by neomycin-like aminoglycoside antibiotics (Moazed et al., 1987, *Nature*, 327:389–94, Woodcock et al., 1991, *EMBO J.*, 10:3099–103) (Neos) and A-and P-site tRNA (Moazed et al., 1986, *Cell*, supra, Moazed et al., 1990, *J. Mol. Biol.*, supra). The positions of the A- and P-site decoding region subdomains, and the identities of post-transcriptionally methylated nucleotides are indicated. The decoding region is drawn with the tertiary base pairs of Gutell and coworkers (Gutell et al., 1985, *Prog. Nucl. Acids Res. Mol. Biol.*, 32:153–216, Gutell, *In The Translational Apparatus*, (Eds. Nierhaus, Subramanian et al.) Plenum Publishing, New York, 1993, pp. 477–88): C1399–G1504, G1401–C1501, C1402–A1500, C1404–G1497, and G1405–C1496. FIG. 1C shows the decoding region oligoribonucleotide analog (SEQ ID NO:1) with nucleotides protected from DMS modification by neomycin and paromomycin (Neos) indicated. The analog contains 16S rRNA decoding region sequences from A1398 to A1410 on the proximal side and U1490 to G1505 on the distal side. The distal end of the analog terminates in the same stem-tetraloop found at the end of the penultimate stem of 16S rRNA (nucleotides 1448–1455). A heterologous clamping helix is shown at the top. Weak and strong protection are indicated by small and large symbols, respectively. FIG. 1D shows the decoding region oligoribonucleotide analog (SEQ ID NO;1) with nucleotides protected from DMS modification, or enhanced in reactivity toward DMS, in response to poly U mRNA and tRNA anticodon stem-loop T7 transcripts. FIG. 1E shows an oligoribonucleotide analog (SEQ ID NO:11) of the A-site of the decoding region, with nucleotides protected from DMS modification by neomycins indicated.

FIG. 2A shows results from DMS probing reactions with the oligoribonucleotide analog alone (lane 6) and in the presence of 0.1, 1, 10, and 100 μM neomycin (lanes 7–10), paromomycin (lanes 11–14), hygromycin (lanes 15–18), streptomycin (lanes 19–22), tetracycline (lanes 23–26), and erythromycin (lanes 27–30). Dideoxy sequencing reactions (lanes 1–4) and a control extension reaction with unmodified RNA (K, lane 5) are to the left, and bands corresponding to nucleotides discussed below are indicated to the right. FIG. 2B shows DMS/N7 probing reactions with the oligoribonucleotide analog alone (lane 1) and in the presence of 0.1, 1, 10, and 100 μM neomycin (lanes 2–5), paromomycin (lanes 6–9).

In FIG. 4A, selectivity of mRNA interactions is shown by DMS probing reactions. Reactions with naked analog (lane 6), 3 μM (lane 7), and 6 μM (lane 8) anticodon stem-loop transcript were repeated in the presence of 2 μg poly U (lanes 9–11), polydeoxy U (lanes 12–14), and poly C (lanes 15–17). Nucleotides protected by tRNA anticodon stem-loop or mRNA are indicated to the right. FIG. 4B shows selectivity of the P-site subdomain for stem-loop structures. DMS probing reactions with naked analog (lane 6), and 1.5, 3, 6, and 12 μM *E. coli* tRNA$^{phe}$ anticodon stem-loop transcript (lanes 7–10), tRNA$^{pro}$ anticodon stem-loop transcript (lanes 11–14), scrambled tRNA$^{phe}$ (sctRNA$^{phe}$, lanes 15–18), tetraloop element (lanes 19–22), and triUloop element (lanes 23–26). Nucleotides protected by the anticodon stem-loops are indicated to the right.

FIGS. 7A and 7B are schematic diagrams of a high-throughput footprinting assay using the analogs of the invention and an oligonucleotide-based reporter system.

FIGS. 8A and 8B are schematic diagrams of a high-throughput footprinting assay using the analogs of the invention and a reverse-transcriptase-based reporter system.

DETAILED DESCRIPTION

Despite the complex structures and numerous associated proteins of complete ribosomes, we have discovered small oligoribonucleotide analogs that mimic small domains of parental RNAs and that can fold and function autonomously for purposes of the screening assays described herein. The invention includes all such autonomously functioning oligoribonucleotide analogs that can be used to identify novel therapeutic agents for antibiotic, antiviral, anti-cancer, anti-proliferative, and anti-inflammatory use, particularly those specifically described below. Other oligoribonucleotide analogs useful as screening probes can be identified in cellular RNA, including mRNA, and viral RNA.

Figure 1A:
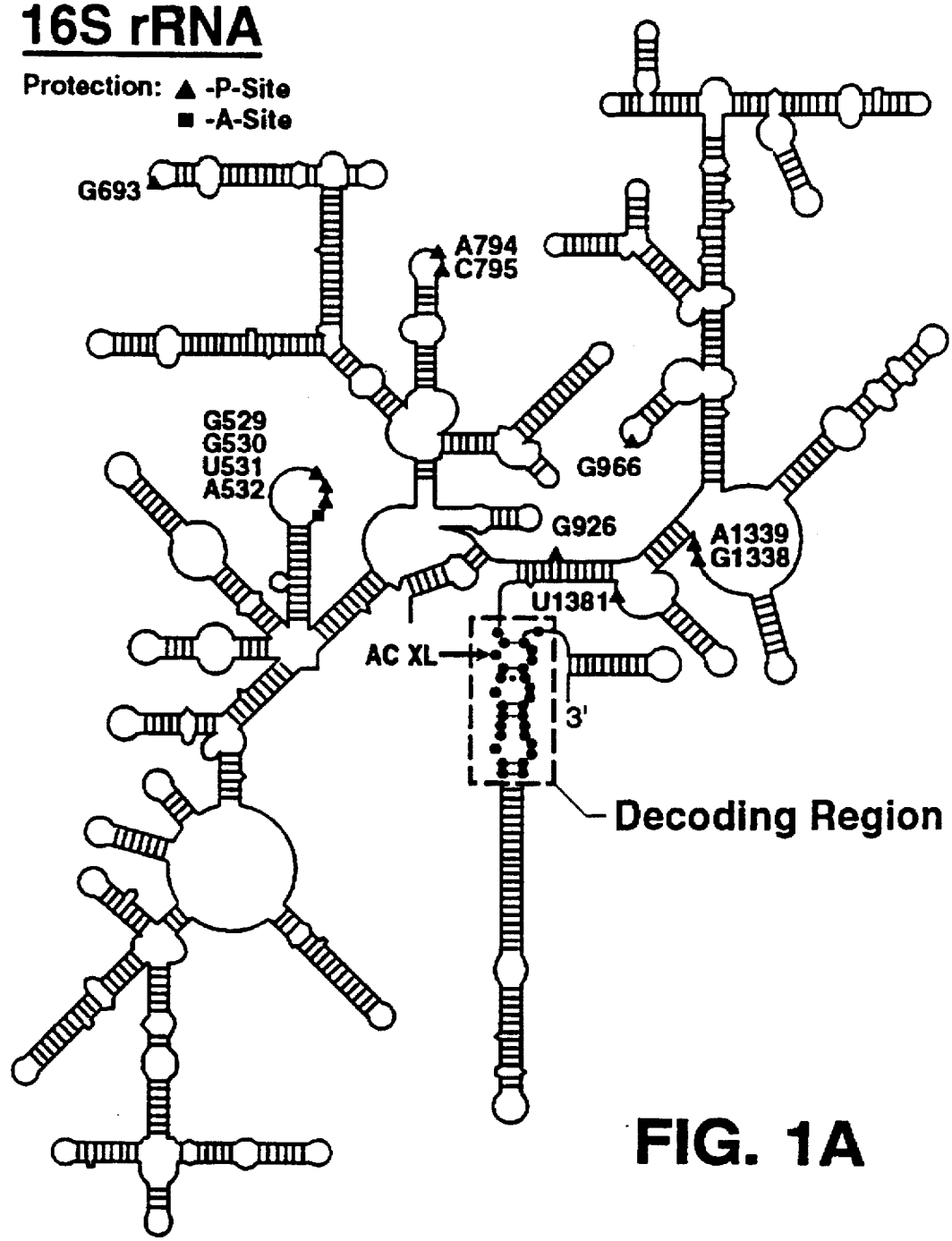

One domain for use to derive the first nucleic acid structure of the analogs is the decoding region of 16S rRNA, which is located near the 3' end of 16S rRNA of *E. coli* (FIGS. 1A and 1B). The experiments described below show that an oligoribonucleotide analog of the decoding region interacts with both antibiotic and RNA ligands of the 30S subunit in a manner that correlates with normal subunit function. The activities of the decoding region analog suggest that the intimidating structural complexity of the ribosome can be, to some degree, circumvented.

Experimental Methods

Preparing an analog

A first oligoribonucleotide analog RNA, derived from the decoding region of 16S rRNA, was made by transcribing, with T7 RNA polymerase (Milligan et al., 1989, *Meth. Enzymol.*, 180:51–62), a linearized pGEM3 plasmid (Promega) as described in Zapp et al., 1993, *Cell*, 74:969–978, containing the analog sequence shown in FIG.

1D (SEQ ID NO:1) flanked by EcoRI and BamHI restriction sites, and a 15 mer reverse primer annealing site immediately 3' of the BamHI site. This sequence includes both the first and second nucleic acid structures to form the complete analog.

Specifically, in the first analog (shown in FIG. 1D), the first nucleic acid structure includes the nucleotide sequences 5'-ACCGCCCGUCACA-3' (SEQ ID NO:12) and 5'-UGAAGUCGUAACAAGG-3' (SEQ ID NO:13) derived from the complete decoding region. The second nucleic acid structure includes a tetraloop 5'-CCUUCGGG-3', which is the minimum size of a tetraloop found to be sufficiently stable, and a nucleotide clamp made of the sequences 5'-GCACAG-3' and 3-CGUGUC-5'. Any other stable helix can be used in place of this particular nucleotide clamp. Likewise, any other stable stem loop can be used in place of this particular tetraloop.

Figure 1D:
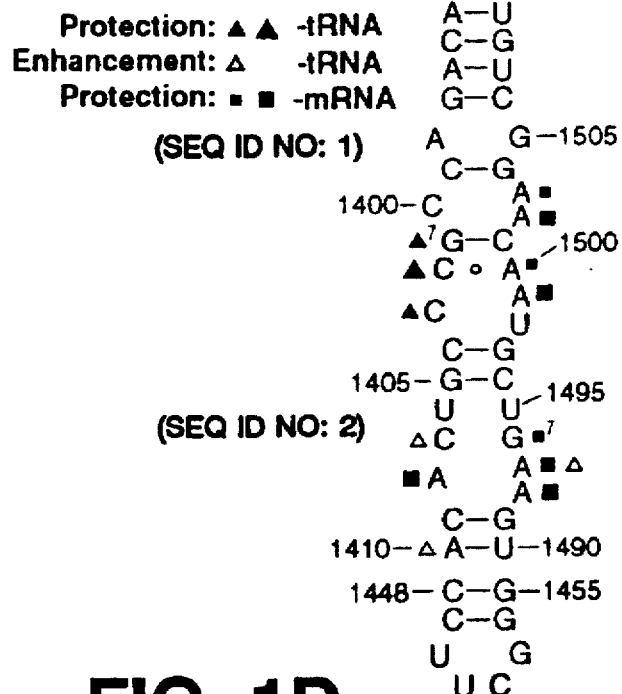
Figure 1E:
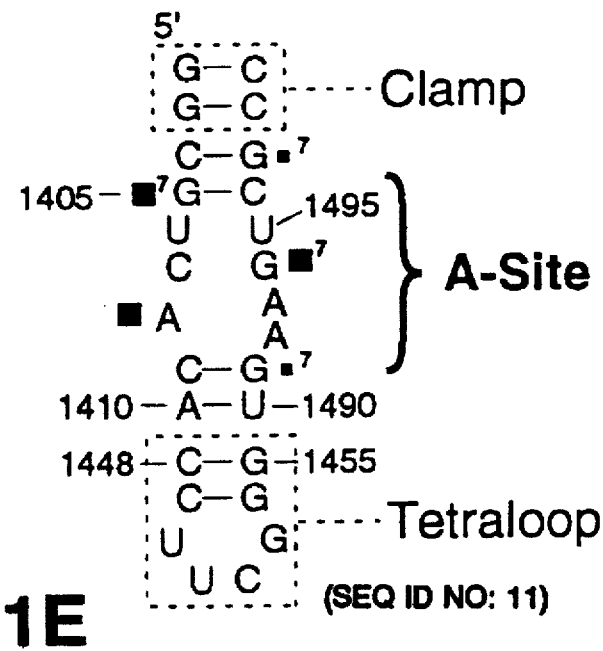

The second analog, shown in FIG. 1E, was made in the same way, but is derived from the A-site subdomain of the decoding region, and has the nucleotides sequences 5'-CGUCACA-3' and 5'-UGAAGGUCG-3'. In terms of the second nucleic acid structure, the second analog has the same tetraloop as in the first analog, but includes a shorter nucleotide clamp made of two nucleotide sequences 5'-GG-3' and 3'-CC-5'. The complete nucleotide sequence of the second analog is 5'-GGCGUCACACCUUCGGGUGAAGUCGCC-3' (SEQ ID NO:11).

Gel purified RNA was concentrated by ethanol precipitation, heated to 80° C. for 1 minute, and immediately placed at 37° C. for 5 minutes.

Aminoglycoside protection experiments

Interaction (or "binding") reactions (12.5 µl) containing 125 ng oligoribonucleotide analog RNA and antibiotics in 80 mM K-Hepes (pH 7.9), 50 mM NH$_4$Cl, and 5% PEG buffer were annealed at 37° C. for 15 minutes and incubated on ice for 1 hour. DMS (1 µl of 1:5 in ethanol) was added, and modification reactions were incubated for 40 minutes on ice. Reactions were stopped with DMS Stop (Peattie et al., 1980, *Proc. Natl. Acad. Sci. USA*, 77:4679–82) and the RNA was purified by ethanol precipitation.

DMS/N7 reactions were performed according to standard protocols (Peattie et al., supra) except that lyophilization steps were replaced by acid-phenol extraction and ethanol precipitation. For primer extension, 10 ng analog RNA was annealed to 0.75 ng end-labeled primer and extended with 10–15 U MoMuLV reverse transcriptase for 1 hour. Reactions were stopped by ethanol precipitation, pellets resuspended in 10 µl 8M urea, 0.05× TBE loading buffer, and 2 µl was loaded onto 8%, 19:1 acrylamide:bisacrylamide, 0.5× TBE sequencing gels.

tRNA protection experiments

Binding reactions were performed as described above for aminoglycoside protection experiments, except that binding buffer contained 200 mM NH$_4$Cl and 80 mM MgCl$_2$. *E. coli* tRNA$^{phe}$ anticodon stem-loop (GGGGAUUGAAAAUCCCC; SEQ ID NO:3) was transcribed with T7 RNA polymerase, gel purified, concentrated by ethanol precipitation, and annealed with a brief heat step (80° C./1 minute followed by 10 minutes on ice).

Selectivity experiments

Reactions were as described for tRNA protection experiments. tRNA$^{pt°}$ anticodon stem-loop (GGUCAUCUUGGGGUGAUGACC; SEQ ID NO:4), scrambled tRNA$^{phe}$ (GGGAGCGUCAUCACAUA; SEQ ID NO:5), tetraloop element (GGGACUUCGGUCCC; SEQ ID NO:6), and triUloop element (GGCGCUUUGCGCC; SEQ ID NO:7) were transcribed and treated as described for the *E. coli* tRNA$^{phe}$ anticodon stem-loop. The assay and results are described below and in FIG. 4B.

Experimental Design and Results

RNA structure analysis with chemical probes is a well established and powerful technique that allows individual atoms of nucleotide bases, or of the phosphodiester backbone, to be monitored for inter- or intra-molecular interactions. For example, dimethyl sulfate (DMS) methylates N1 of A, N7 of G, and N3 of C residues, kethoxal (KE) forms an adduct with N1 and N2 of G, and a soluble carbodiimide (1-cyclohexyl-3-(2-morpholinoethyl) carbodiimide metho-p-toluene sulfonate, CMCT) modifies N3 of U residues. Nucleotide base modifications that interfere with formation of Watson-Crick base pairs are typically monitored via reverse transcription, as the progress of the reverse transcriptase enzyme is strongly impeded when it encounters such modifications. This leads to production of a truncated reverse transcription product whose length effectively maps the position of the modified base in the RNA chain when the products are run on standard DNA sequencing gels.

Other modifications that do not themselves directly interfere with formation of Watson-Crick base pairs can be similarly monitored, by first inducing RNA strand scission. For example, methylation of N7 of G by DMS can be monitored by treating the methylated RNA with sodium borohydride and aniline to induce strand scission at the positions of N7 methylation. Reverse transcriptase simply falls off the template at these points, again leading to a truncated product that maps the position of N7 methylation.

We used these principles and techniques to analyze the oligoribonucleotide analogs of the invention and to develop screening assays using these analogs.

We first designed an oligoribonucleotide analog of the decoding region shown in FIGS. 1C and 1D (SEQ ID NO;1) as described above, and asked if it could interact with aminoglycoside antibiotics such as neomycin, which have previously been shown to protect N1 of A1408 (this notation indicates the adenine at location 1408) and N7 of G1491 and G1494 within the A-site subdomain of the decoding region (Moazed et al., 1987, *Nature*, supra; Woodcock et al., supra); similar interactions with the analog would be a strong indicator of its proper folding and functional potential. Conversely, other antibiotics, such as streptomycin, tetracycline, and erythromycin interact with other segments of 16S rRNA or 23S rRNA (Moazed et al., 1987, *Nature*, supra; Woodcock et al., supra, Moazed et al., 1987, *Biochimie*, 69:879–84) and would not, therefore, be expected to interact with the analog. A second analog, derived from the A-site subdomain of the decoding region (and shown in FIG. 1E), was tested in the same way.

As summarized in FIGS. 1C, 1D, and 1E, the interactions of aminoglycosides such as neomycin and paromomycin with decoding region oligoribonucleotide analogs bear a striking similarity to their counterpart interactions with the decoding region in subunits of complete 16S rRNA in ribosomes. In particular, the decoding region of ribosomes (FIG. 1A) and a small analog containing just the A-site subdomain (FIG. 1E) exhibit virtually identical aminoglycoside interactions, which are abolished by a single G to U transversion at position 1491.

Figure 2A:
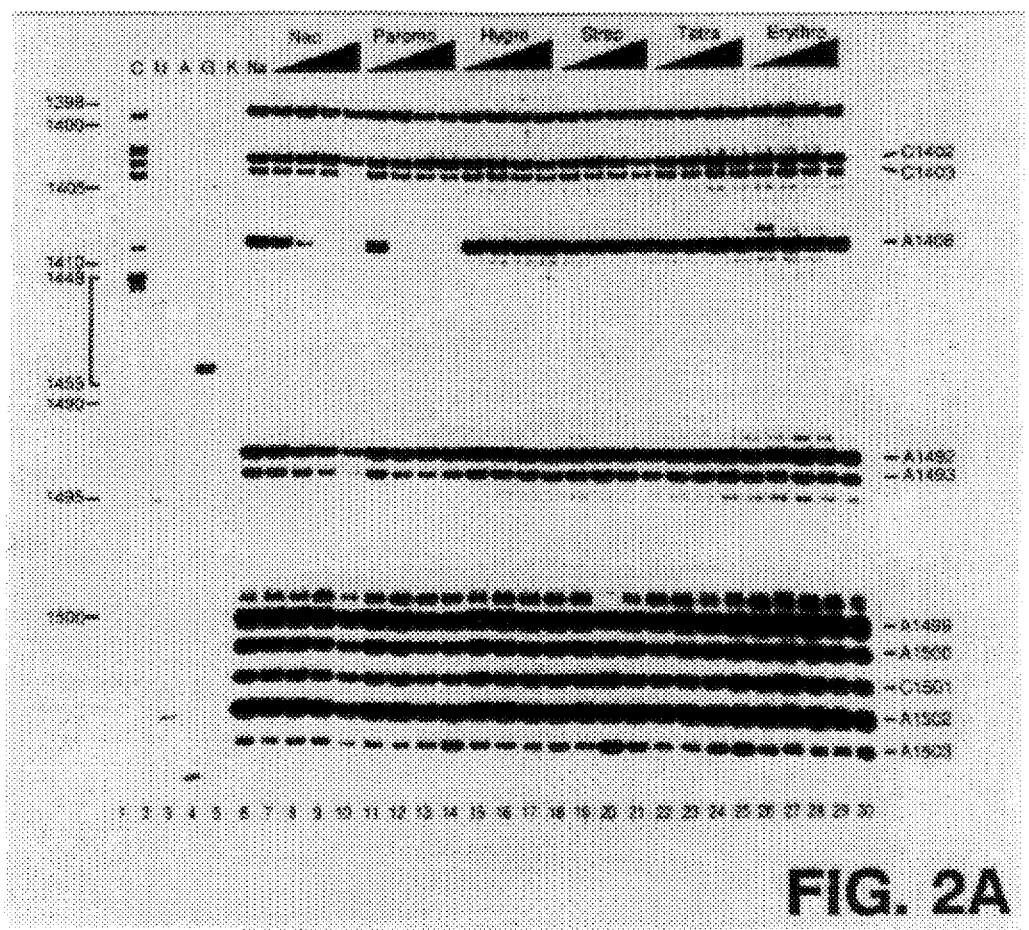
FIGS. 2A–2B are photos of electrophoresis gels showing decoding region analog-antibiotic interactions.

The analogs were probed with dimethyl sulfate (DMS; Stern et al., 1988, *Meth. Enzymol.*, 164:481–89) alone as naked RNA, or in the presence of increasing concentrations of neomycin, paromomycin, hygromycin, streptomycin, tetracycline, and erythromycin. FIG. 2A shows that neomycin (lanes 7–10) and the closely related aminoglycoside paromomycin (lanes 11–14) strongly protected N1 of A1408 at concentrations of 10 and 1 µM, respectively. In addition, hygromycin (lanes 15–18), a structurally dissimilar aminoglycoside, weakly enhanced the reactivity of N1 of A1408. In contrast, streptomycin (lanes 19–22), tetracycline (lanes 23–26), and erythromycin (lanes 27–30), antibiotics that do not interact with the decoding region in 16S rRNA, did not detectably interact with the analogs.

Figure 2B:
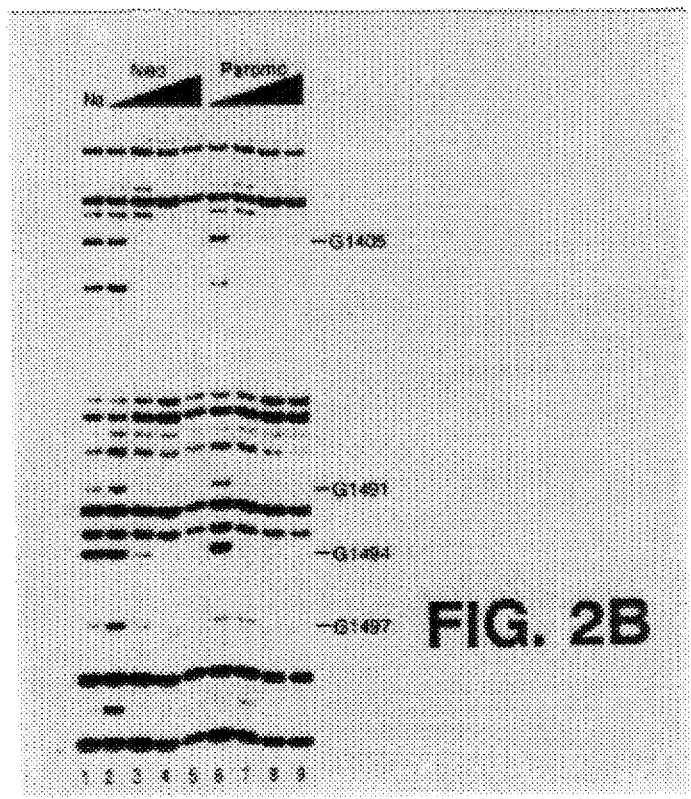

FIG. 2B shows that, in addition to N1 of A1408, N7 of G1405 and G1494 were strongly protected by neomycin and paromomycin, while N7 of G1491 and G1497 were weakly protected. These data are summarized in FIG. 1C. Because these results closely match those previously obtained with antibiotics and intact, whole ribosomes (Moazed et al., 1987, *Nature*, supra, Woodcock et al., supra, Moazed et al., 1987, *Biochimie*, supra), we concluded that the A-site subdomain of our oligoribonucleotide analog folds into a biologically relevant conformation.

Figure 3:
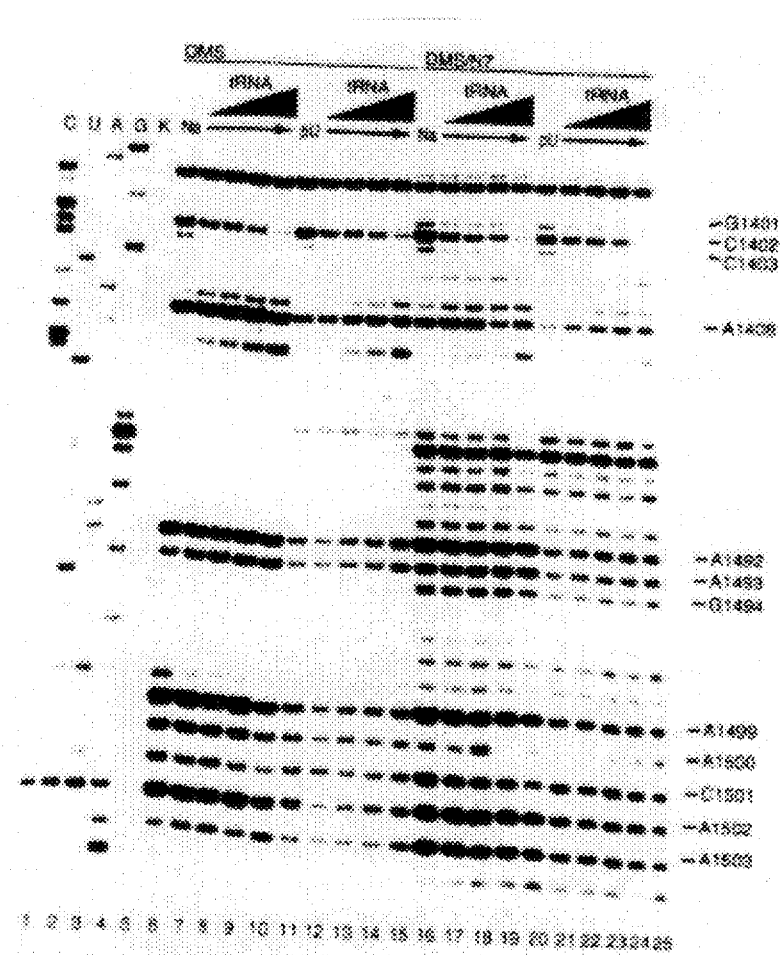
FIG. 3 is an electrophoresis gel showing interactions of tRNA anticodon stem-loop transcripts and poly U with the decoding region oligoribonucleotide analog. DMS and DMS/N7 probing reactions with naked analog (lanes 6 and 16), and 3, 6, 12, and 24 μM anticodon stem-loop transcript (lanes 7–10 and 12–15). The same reactions were repeated in the presence of 4 μg poly U (lanes 11–15 and 21–25).

We asked next if the analog could function similarly to the decoding region of 16S rRNA in the ribosome by interacting with tRNA and/or mRNA. In the experiment shown in FIG. 3, increasing concentrations of a minimal tRNA for these purposes (Rose et al., 1983, *J. Mol. Biol.*, 167:103–17), a T7 transcript of the anticodon stem-loop of *E. coli* tRNA$^{phe}$, were incubated either alone (lanes 7–10 and 17–20) or in the presence of cognate poly U message (lanes 11–15 and 21–25). FIG. 3 shows that the anticodon stem-loop transcript protected N3 of C1402 and C1403 (compare lane 6 with lanes 7–10) and N7 of G1401 (compare lane 16 with lanes 17–20), while poly U protected N1 of A1408, A1492, A1493, A1499, and A1502 strongly, N1 of A1500, A1503 weakly, and N7 of G1494 weakly (compare lane 6 with lanes 11–15 and lane 16 with lanes 21–25). In addition, the reactivities of N1 of A1410 and A1493, and N3 of C1407 were enhanced by the stem-loop (compare lane 6 with lanes 7–10), effects which were attenuated in the presence of poly U (compare lanes 7–10 with lanes 12–15).

Comparison of the present results with data from previous studies with ribosomes (Moazed et al., 1986, *Cell*, supra; Moazed et al., 1990, *J. Mol. Biol.*, supra) shows that the nucleotides protected by the tRNA anticodon stem-loop transcript in the analog (G1401, C1402, and C1403) are closely associated with, and in fact overlap, those protected by P-site bound tRNA in the presence or absence of message (C1399, C1400, and G1401). Furthermore, within the A-site subdomain of the analog, nucleotides protected by mRNA (A1408, A1492-G1494) are identical to those associated with the mRNA-dependent interaction of tRNA with the A-site of ribosomes (Moazed et al., 1986, *Cell*, supra; Moazed et al., 1990, *J. Mol. Biol.*, supra). The other nucleotides, protected by mRNA (A1499, A1500, A1502, and A1503), have not been previously identified with either A- or P-site function in chemical probing experiments.

Figure 4A:
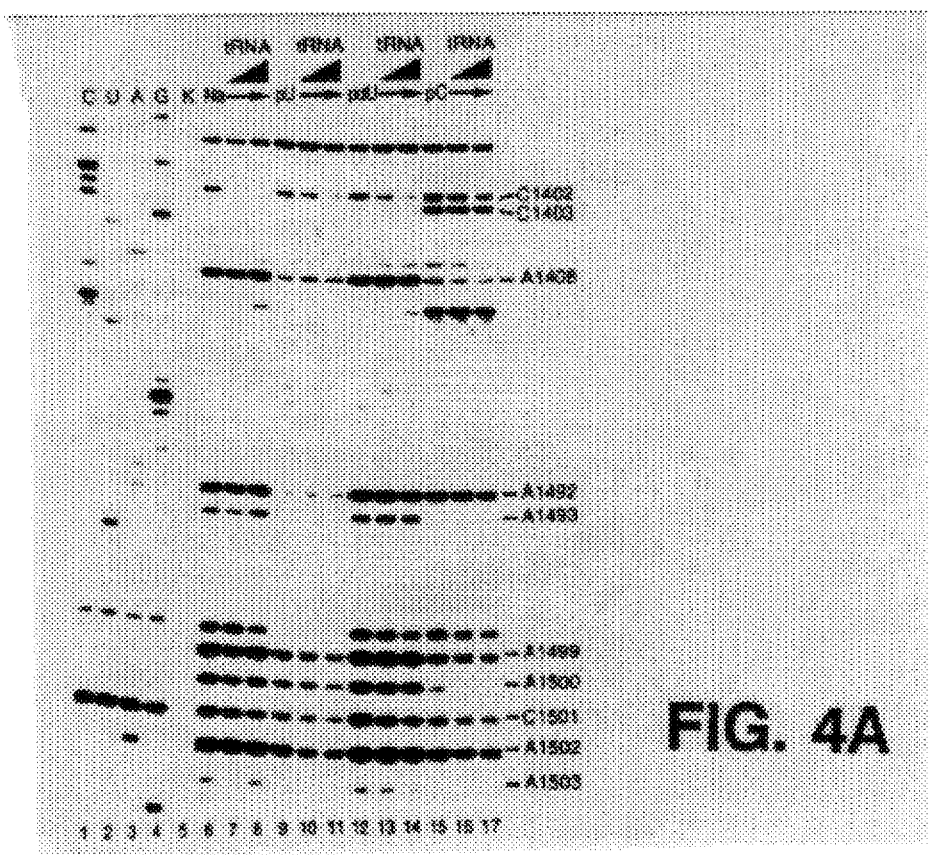
FIGS. 4A–4B are electrophoresis gels showing the selectivity of decoding region analog interactions.

To help determine whether poly U mRNA interactions were mediated by Watson-Crick base pairs with A residues in the analog, we next tested poly C, an mRNA with no potential to form Watson-Crick base pairs with A residues, and with polydeoxy U, a 2'-deoxy-form of poly U, with similar Watson-Crick base pairing potential. The experiment of FIG. 4A showed that while poly U protected A1408, A1492, and A1493 strongly as expected (compare lanes 6–8 with lanes 9–11), polydeoxy U failed to detectably interact with any nucleotides in the analog (compare lanes 6–8 with lanes 12–14). The interactions of poly C were more complex, as the reactivities of N1 of A1410 and N3 of C1402 and C1403 were enhanced (compare lanes 6–8 with lanes 15–17). However, with the exception of A1492, poly C protected the same nucleotides as poly U, including A1408, A1493, A1499, A1500, A1502, and A1503. Thus, despite the apparent disruption of analog structure induced by poly C, its protection pattern was virtually identical to that of poly U. Considered together, these results suggest that the interactions of mRNA with the decoding region are not mediated simply by Watson-Crick base pairing.

C1402 and C1403 are unreactive in 16S rRNA (Moazed et al., 1986, *J. Mol. Biol.*, 187:399–416); their reactivity in the analog and their protection by the tRNA anticodon stem-loop transcript suggest that the structure of the P-site subdomain of the oligoribonucleotide analog differs from that of ribosomes.

To understand better the discriminatory capacity, or selectivity, of the P-site subdomain of the oligoribonucleotide analog, we asked next whether it differentiates between closely related RNA structures. In the experiment shown FIG. 4B, a second (sequence-divergent), proline-specific tRNA anticodon stem-loop (tRNA$^{pro}$) (GGUCAUCUUGGGGUGAUGACC; SEQ ID NO:4), a scrambled-sequence *E. coli* tRNA$^{phe}$ with little potential for secondary structure formation (sctRNA$^{phe}$) (GGGAGCGUCAUCACAUA; SEQ ID NO:5), a highly stable tetraloop stem-loop element (tetraloop) (GGGACUUCGGUCCC; SEQ ID NO:6), and another, smaller stem-loop element with a loop composed of only three U residues (triUloop)(GGCGCUUUGCGCC; SEQ ID NO:7) were each titrated into a binding reaction with the analog.

Figure 4B:
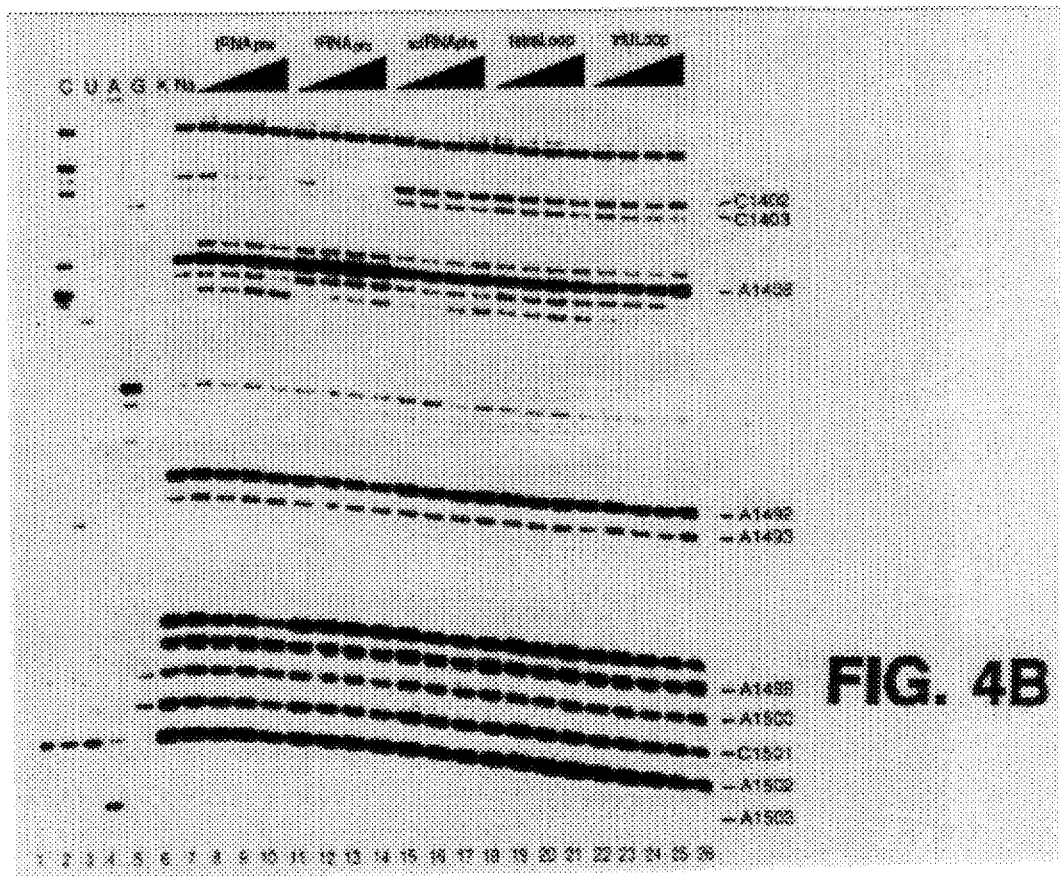

FIG. 4B shows that only the tRNA$^{phe}$ and tRNA$^{pro}$ anticodon stem-loop transcripts interacted, each strongly protecting C1402 and C1403. The failure of the scrambled tRNA$^{phe}$ and other stem-loop elements to interact detectably supports the hypothesis that, despite its altered conformation, the P-site subdomain interacts selectively with RNA ligands. These results suggest, therefore, that the P-site subdomain of the oligoribonucleotide analog exhibits significant discriminatory capacity that may be related to ribosomal P-site function.

In light of the omission of 1500 nucleotides of the complete 16S rRNA, all nucleotide modifications, and the 21 small subunit proteins normally found in the 30S ribosomal subunit, the demonstration of interactions between the small decoding region oligoribonucleotide analog and 30S subunit ligands that correlate with normal 30S subunit activities was surprising and unexpected. Positive correlations are probably best exemplified by the interactions of the antibiotics with the A-site subdomain where a nearly perfect correspondence between the characteristics of the decoding region in ribosomes and the oligoribonucleotide analog was observed with a wide variety of compounds.

Uses/Advantages of the Invention

The oligoribonucleotides of the invention are diverse, in that they can be derived from any ribosomal RNA (e.g., 16S, 23S), human immunodeficiency virus (HIV) RNA (see Green (1993) *AIDS Res. Rev.* 3:41–55 for examples of desirable regions such as Tat or Rev interaction sites), or any other RNA which can be manipulated to retain a functionally relevant structure. Although the decoding region of 16S rRNA and aminoglycoside antibiotics are featured in the experiments described herein, they are not the only region or chemical class which can be used in this invention.

For example, messenger RNA regulatory elements, telomerase RNA (see, e.g., Bahattacharyya and Blackburn, *EMBO J.*, 13:5721–31, 1994), oncogene mRNAs, cytokine and lymphokine mRNAs, thymidylate synthase mRNAs, and various viral elements such as the adenovirus late mRNA tripartite leader, hepatitis delta virus RNA, and picornavirus "ribosomal landing pads," or "internal ribosomal entry sites," located in the 5' untranslated region, can also be used to design oligoribonucleotide analogs of the invention.

Moreover, self-splicing group I introns, including the HDV group I intron, are inhibited by the binding of aminoglycosides, and thus can be used to design RNA oligoribonucleotide analogs. Furthermore, the HIV Rev-Response-Element (RRE) is bound by some of the same antibiotics that bind to the decoding region of 16S rRNA. Neomycin binding to the RRE inhibits Rev function and viral replication in model cell culture systems. Thus, the RRE is a suitable target for designing oligoribonucleotide analogs that are useful to assay antibiotics effective against the RRE.

Any known RNA structural motif can be used as parental RNA to design an oligonucleotide analog that can be used as a screening target, and because the transport, processing, and translation of mRNA depend on such structures and their interactions with various binding partners, a large array of potential targets in viral and cellular mRNA exist. Extending these ideas even further, if one assumes that mutant cellular mRNA sequences produce altered mRNA structures, it may even be possible to selectively target specific mutant mRNA sequences with small molecules.

In addition to the first nucleotide sequences derived from the parental RNA, the oligoribonucleotide analogs of the invention also contain second, heterologous sequences (e.g., artificial stem loops and nucleotide clamps) that promote the appropriate three-dimensional conformation of the first nucleotide sequences for normal molecular interactions with candidate drugs, nucleic acid molecules, etc. The small size of these candidate drugs and molecules makes them amenable to numerous inexpensive in vitro assays that use a variety of oligoribonucleotide analogs.

Protein synthesis inhibitors have two main ribosomal targets: the decoding region of 16S rRNA, and the peptidyl transferase region (Domain V) of 23S rRNA. Aminoglycosides interact with the decoding region while MLS antibiotics (macrolides, lincosamides, and streptogramins) interact with the peptidyl transferase region. Peptides, nucleic acid molecules, and a variety of other chemical compounds and molecules may be useful as therapeutics, and can easily be screened using the oligoribonucleotide analogs and methods of this invention.

The oligoribonucleotide analogs enable the use of improved methods to screen for novel therapeutic compounds, particularly antibiotic compounds that inhibit protein synthesis. Standard methods to screen antibiotics involve detecting antimicrobial or bactericidal activity in cultured cells over long time periods (up to several days). Screening many potential antibiotic compounds under these conditions can be expensive and time consuming. On the other hand, screening assays using the oligoribonucleotide analogs of the invention have several distinct advantages over these known screening methods.

The new screening assays are much more rapid (an assay according to the invention can be carried out in about an hour), the individual assays require only small amounts of materials (volumes of about 100 µl), and numerous reactions can be carried out in parallel (e.g., in a 96 well microtiter plate). Using the methods of the invention, likely candidate compounds can be rapidly identified, and only the likely candidates then could be further tested with cell culture assays.

Some of the advantages derive from the analogs themselves compared to full-sized ribosomes. The oligoribonucleotide analogs are small enough to be easily produced, either enzymatically as T7 polymerase transcripts, or chemically by automated RNA synthesis. The analogs are far more stable than ribosomes because they are radically simpler. Furthermore, unlike ribosomes, their labile ribophosphodiester backbone can be stabilized by incorporation of 2'-O-methyl ribonucleotides, deoxyribonucleotides, or phosphorothioates, either uniformly or at selected positions.

In addition, analogs can be readily derivatized during automated chemical synthesis. For example, fluorescent moieties can be introduced at either termini (5' or 3'), or internally, and coupling moieties, such as primary amines or biotin, can be introduced at either termini (see discussion below). Further, the detection of interactions between new test compounds and analogs is more likely to be relevant to potential antibiotic activity, because, unlike ribosomes, the new analogs present a small, well-defined target.

Screening Assays

No particular class of molecular structure is selected by the following screening methods. Rather, the methods select only for the existence of highly specific interactions involving particular nucleotide atoms in the analog RNA target. Therefore, specific compounds can be tested to determine whether they are likely to have antibiotic activity.

General Considerations

Aminoglycosides are polycations and charge-charge interactions with the negatively charged phosphodiester backbone of the oligoribonucleotide analogs are likely important determinants of their binding specificity and affinity. Thus, important factors governing the formation and stability of aminoglycoside-RNA interactions include mono- and divalent-cation (salt) concentrations, and the presence or absence of nonspecific nucleic acids. Accordingly, low salt concentrations (<100 mM K+, NH4+, Na+, <5 mM Mg++) favor complex formation, and the presence of nonspecific nucleic acids disfavor it. Candidate compounds to be tested should, therefore, be prepared in low salt buffers largely free of contaminating nucleic acids.

To facilitate high throughput screening, a standard microtiter plate format with a standard fluorescence or radiation detector is used. A robotic system is used to load, wash, and detect a signal in each well. Cation concentrations, nonspecific nucleic acids, and other variables including temperature and time can be adjusted during binding and washing stages to adjust background binding levels.

Three Screening Methods

Figure 5A:
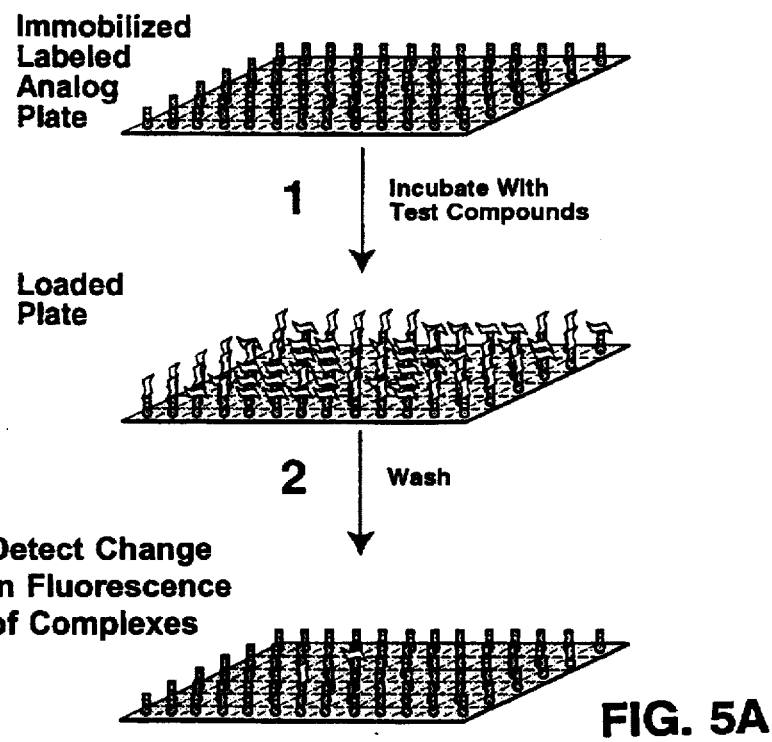
FIGS. 5A and 5B are schematic diagrams of two different screening methods using the oligoribonucleotide analogs of the invention.
Figure 5B:
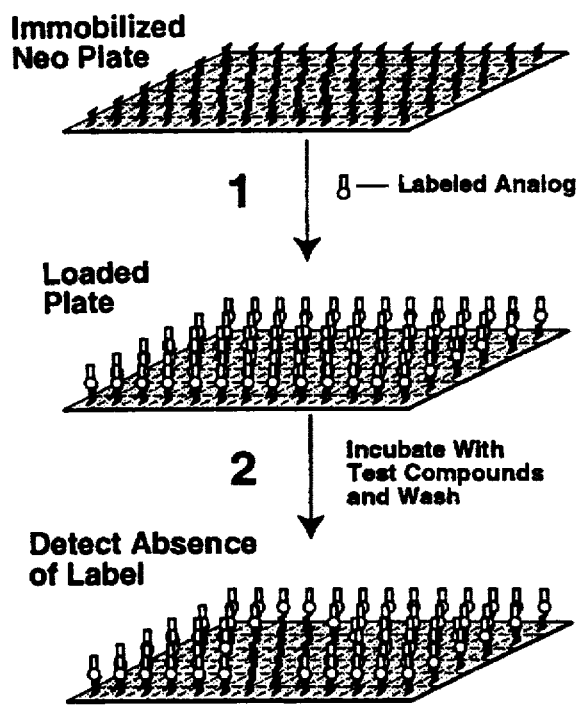

FIGS. 5A and 5B illustrate two specific screening assays based on 1) binding of test compounds to an immobilized (naked) oligoribonucleotide analog functioning as a reporter ("affinity assay"), and 2) displacement of a prebound reporter molecule from an immobilized analog by test compounds ("competitive binding assay"), respectively. These two methods, while distinct, are related in their overall strategy and organization. A third method (FIGS. 7A, 7B, 8A, and 8B), based on oligomer binding to an in situ footprinted analog, differs in its organization and strategy from the first two methods, and will be discussed separately.

Method 1:

Affinity Assay

Figure 6:
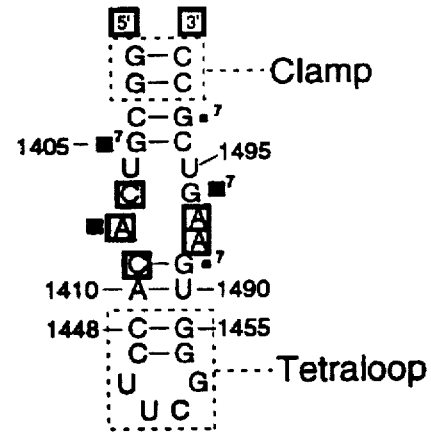
FIG. 6 is a schematic diagram of an analog of the A-site of the decoding region, and shows the potential nucleotide locations (boxes) for derivatization, e.g., to add a fluorescent label.

This screening method can be implemented with an immobilized, fluorescently labeled oligoribonucleotide analog, as shown in FIG. 5A. The method consists of (1) incubation of the immobilized analog with test compounds, (2) wash step(s), and subsequent detection of complex formation relying on changes in the fluorescence properties of the immobilized RNA analog. The RNA analog can be derivatized, e.g., during automated chemical synthesis, both for immobilization and for labelling. Possible positions for derivatization on an oligoribonucleotide analog are indicated by boxes around the nucleotides in FIG. 6.

For example, for immobilization, the analog can be derivatized with either terminal biotin (using biotin phosphoramidite (5'-biotin) or CPG (3'-biotin)), or a free primary amino group (using amino modifier phosphoramidite (5'-NH2) or CPG (3'-NH2)). Immobilization in microtiter plate wells can then be accomplished with polystyrene plates activated with streptavidin or maleic anhydride, respectively. After coupling, plates should be thoroughly washed to eliminate soluble analog RNA.

For labelling, analogs are derivatized to allow the addition of a fluorophore at one of the RNA termini with fluorescein phosphoramidites (3' labeling) or CPG (5' labeling), or the incorporation of fluorescent adenosine or cytosine nucleotides (with EthenoA and EthenoC phosphoramidites, respectively) at specific internal positions in the RNA. The latter approach can be much more sensitive, due to the proximity of the fluorophore and antibiotic binding site. Alternatively, a fluorescent dye such as ethidium bromide, or possibly Hoechst 33258, can be used with underivatized RNA. This labelling allows the detection of any changes in either the binding or fluorescent properties of the dye, or both, upon test compound-analog complex formation.

Typical (solution) binding reactions contain 25 mM neutral pH buffer (Tris or Hepes) and 50 mM monovalent salt (KCl, NH4Cl, etc). It is advantageous to carry out binding reactions at 30°–37° C. for approximately 30 minutes to facilitate the simultaneous annealing of the RNA. Washes can utilize the same buffer.

Test compound and salt concentrations should be adjusted empirically to optimize the assay. For example, the test compound concentration should be in the micromolar range, and salt concentrations should be in the range of 10 to 500 mM, but these numbers must be adjusted depending on the particular assay conditions. In addition, nonspecific nucleic acids can be added to the binding step to reduce the effects of any contaminating compounds with nonspecific affinity for nucleic acids. For example, the nonspecific nucleic acid could be total yeast tRNA, poly 1-C, etc. Another potentially useful nonspecific nucleic acid would be (soluble) A-site analog carrying the G1491U point mutation.

Method 2:
Competitive Binding Assay

As shown in FIG. 5B, this screening method is based on the hypothesis that useful test compounds will displace prebound soluble reporter ligands from their immobilized analog binding sites. For example, immobilized neomycin (an antibiotic ligand known to bind to analogs derived from the decoding region of 16S rRNA) can be (1) pre-loaded with a labeled analog, and (2) test compounds added and allowed to compete with immobilized neomycin for the labeled analog, which serves as the reporter. After a wash step to remove any displaced analog, still complexed with the test compound, detection of the absence of label in specific wells would indicate that specific test compounds bound the analog RNA efficiently, a positive result. The reciprocal configuration, with immobilized analog RNA and labeled neomycin, can also be used.

Neomycin and other aminoglycosides contain numerous primary amino groups that are ideal targets for coupling to either amine-reactive fluorescent probes or activated polystyrene. For example, a soluble neomycin reporter molecule can be produced by coupling neomycin to NHS-Fluorescein.

In the alternative, neomycin can be immobilized on maleic anhydride-activated polystyrene microtiter plates. As discussed above, the oligoribonucleotide analog can be similarly labeled or immobilized.

Method 3:
Screening By In situ Footprinting

FIGS. 7A and 7B, and 8A and 8B, illustrate a third screening method based directly on our chemical probing experience which has shown that the N1 atom of A1408 is strongly methylated by DMS in the absence of neomycin, and conversely, is strongly protected from DMS methylation in the presence of neomycin. In conventional footprinting experiments, this differential modification provides a method for detection of complex formation (monitored by inhibition of primer extension). Method 3 similarly exploits differential methylation, but monitors this methylation, e.g., via the differential annealing of a labeled complementary oligomer (e.g., CAGUGU) with a binding site overlapping the site of methylation, A1408 (FIGS. 7A and 7B).

In this method, the N1 atom of A1408 is strongly methylated by dimethyl sulfate (DMS) in the absence of neomycin (FIG. 7A) and, conversely, strongly protected from DMS methylation in the presence of neomycin ("bound small molecule") (FIG. 7B). Thus, after complex formation (step 1) and DMS modification (step 2), the methylation state of A1408 reflects its (previous) involvement in complex formation with neomycin.

The mechanics of the assay are similar to Method 1 in that the first step involves forming complexes between the immobilized (but here unlabeled) analog and test compounds (Step 1). After complex formation and washing steps, the plate is treated with DMS to differentially methylate the RNA (Step 2). DMS reactions are then stopped with a 1M βME wash, and labeled reporter oligo added and annealed (Step 3).

The technique for monitoring differential methylation illustrated in FIGS. 7A and 7B relies on the inability of N1-methylated A to form Watson-Crick base pairs with a short labeled oligomer. In FIG. 7A, with uncomplexed analog and methylated N1, the short oligo fails to anneal to the analog and is washed away, leaving no label in that well. In FIG. 7B, with complexed analog and unmethylated N1, the oligo anneals to the analog and is effectively immobilized on it, leaving label in the well. Wells that retain the reporter oligo indicate that A1408 was not methylated, which in turn indicates that A1408 was protected by a bound antibiotic ligand. Thus, the presence of label in a well constitutes a positive result.

An alternative technique for monitoring differential methylation shown in FIGS. 8A and 8B relies on reverse transcription of the modified template. Steps 1 and 2 are identical to those shown in FIGS. 7A and 7B, except that the target analog (RNA) is no longer immobilized. Instead, a biotinylated primer (e.g., having the nucleotide sequence TTCACCCGGAAGGTG; SEQ ID NO:12) is added to each reaction (FIGS. 8A and 8B), and primer extension is initiated in the presence of labeled TTP (e.g., $\alpha$-$^{32}$P-TTP) and reverse transcriptase.

In FIG. 8A, primer extension is inhibited by methylation of N1 of A1408 and no label is incorporated. In FIG. 8B, primer extension is successful, resulting in the incorporation of label into the primer. In both cases the biotinylated primer is immobilized via interaction with streptavidin-coated wells. After a wash step to remove unincorporated labeled TTP, only the scenario in FIG. 8B will allow retention of the label in the well, thus reporting the presence of a bound ligand in step 1.

The reverse-transcriptase-based reporter methodology superficially resembles standard chemical probing methods. The main difference, aside from the immobilized primer, is that the primer extension conditions, e.g., Mg concentration, reaction time, temperature, and amount of enzyme, are adjusted, using standard techniques, such that methylation of A1408 will completely stop extension of a high percentage (approximately 90%) of the transcripts. This is the opposite of the desired situation in standard experiments, where conditions are adjusted such that greater than 90% of the transcripts are full-length.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An artificial oligoribonucleotide analog having both natural and heterologous sequences contained therein, wherein said artificial oligoribonucleotide analog has a three dimensional structure that mimics a ligand binding region of a larger parental RNA molecule, said artificial oligoribonucleotide analog comprising;

a first oligoribonucleic acid structure whose sequence is identical to the sequence of said ligand binding region; and a second nucleic acid structure consisting of a heterologous sequence that does not exist adjacent to the sequence of said ligand binding region in said parental RNA molecule; wherein
    i) the conformation of said second nucleic acid structure is not naturally present adjacent to said ligand binding region;
    ii) said second nucleic acid structure stabilizes the conformation of said first oligoribonucleic acid structure so as to mimic the conformation of said parental RNA molecule ligand binding region so that said first oligoribonucleic acid structure binds said ligand with a binding pattern substantially identical to said parental RNA molecule binding pattern; and
    iii) said first and second structures are linked by one or more covalent or non-covalent bonds.

2. An artificial oligoribonucleotide analog of claim 1, wherein the sequence of said first nucleic acid structure is identical to a ligand binding region of a 16S ribosomal RNA (rRNA).

3. An artificial oligoribonucleotide analog of claim 2, wherein said ligand binding region comprises the decoding region of 16S rRNA.

4. An artificial oligoribonucleotide analog of claim 3, wherein said ligand binding region comprises nucleotides 1398–1410 and 1490–1505 of 16S rRNA.

5. An artificial oligoribonucleotide analog of claim 3, wherein said ligand binding region comprises the A site subdomain of the decoding region of 16S rRNA.

6. An artificial oligoribonucleotide analog of claim 5, wherein said ligand binding region comprises nucleotides 1404–1410 and 1490–1497 of 16S rRNA.

7. An artificial oligoribonucleotide analog of claim 1, wherein said second nucleic acid structure comprises a tetraloop.

8. An artificial oligoribonucleotide analog of claim 7, wherein said tetraloop comprises the nucleotide sequence:

5'-CCUUCGGG-3'.

9. An artificial oligoribonucleotide analog of claim 1, wherein said second nucleic acid structure comprises two nucleotide sequences forming a based-paired nucleotide clamp.

10. An artificial oligoribonucleotide analog of claim 9, wherein said base-paired nucleotide clamp comprises the nucleotide sequence:

3'-CGUGUC-5'

5'-GCACAG-3'.

11. An artificial oligoribonucleotide analog of claim 9, wherein said base-paired nucleotide clamp comprises the nucleotide sequence:

3'-CC-5'

5'-GG-3'.

12. An artificial oligoribonucleotide analog of claim 1, wherein the sequence of said first oligoribonucleic acid structure is identical to a decoding region of 16S rRNA, and said second nucleic acid structure comprises a tetraloop and a base-paired nucleotide clamp.

13. An artificial oligoribonucleotide analog of claim 12, wherein said decoding region comprises nucleotides 1398–1410 and 1490–1505 of 16S rRNA, said tetraloop comprises the nucleotide sequence 5'-CCUUCGGG-3', said base-paired nucleotide clamp comprises the nucleotide sequence:

3'-CGUGUC-5'

5'-GCACAG-3', and the complete linear nucleotide sequence of said combined first and second nucleotide structures of said analog is 5'-GCACAGACCGCCCGUCACACCUUCGGGUGAAG-UCGUAACAAGGCUGUGC-3' (SEQ ID NO:1).

14. An artificial oligoribonucleotide analog of claim 12, wherein said decoding region comprises nucleotides 1404–1410 and 1490–1497 of 16S rRNA, said tetraloop comprises the nucleotide sequence 5'-CCUUCGGG-3', said base-paired nucleotide clamp comprises the nucleotide sequence:

3'-CC-5'

5'-GG-3', and the complete linear nucleotide sequence of said combined first and second nucleotide structures of said analog is 5'-GGCGUCACACCUUCGGGUGAAGUCGCC-3' (SEQ ID NO:11).

15. A binding assay for determining the potential therapeutic activity of a test compound, said assay comprising the steps of mixing a test compound with an artificial oligoribonucleotide analog of claim 1 under conditions that allow formation of a binding complex between said analog and said test compound, and detecting the formation of a binding complex, wherein the presence of a binding complex indicates that said test compound has potential therapeutic activity.

16. A method of claim 15, wherein said artificial oligoribonucleotide analog is labelled and immobilized on a surface, and said binding complex is detected by monitoring changes in the signal of said label when a test compound is bound to said analog.

17. A method of claim 15, wherein said artificial oligoribonucleotide analog is immobilized on a surface, said test compound is labelled, and said binding complex is detected by detecting said label bound to said immobilized analog.

18. A method of claim 16, wherein said artificial oligoribonucleotide analog is fluorescently or radioactively labelled.

19. A competitive binding assay for determining the potential therapeutic activity of a test compound, said assay comprising the steps of mixing an artificial oligoribonucleotide analog of claim 1 with an analog-binding ligand under conditions that allow formation of a first binding complex between said analog and said ligand, mixing a test compound with the first binding complex under conditions that allow said test compound to disrupt said first binding complex to form a second binding complex between said analog and said test compound, and detecting the disruption of the first binding complex, wherein the disruption of the first binding complex indicates that said test compound has potential therapeutic activity.

20. A method of claim 19, wherein said ligand is labelled, said artificial oligoribonucleotide analog is immobilized on a surface, and the disruption of the first binding complex is detected by monitoring any decrease in the signal of said label when a test compound displaces said ligand from said first binding complex.

21. A method of claim 19, wherein said artificial oligoribonucleotide analog is labelled, said ligand is immobilized on a surface, and the disruption of the first binding complex is detected by monitoring any decrease in the signal of said label when a test compound displaces said analog from said first binding complex.

22. A method of claim 21, wherein said artificial oligoribonucleotide analog is fluorescently or radioactively labelled.

23. A method of claim 21, wherein said ligand is fluorescently or radioactively labelled.

24. An in situ footprinting assay for determining the potential therapeutic activity of a test compound, said assay comprising the steps of mixing an artificial oligoribonucleotide analog of claim 1 with a test compound under conditions that allow formation of a binding complex between said analog and said test compound, incubating said binding complex with a chemical probing reagent and monitoring for an effect of said reagent on said analog in said complex, in a separate control reaction, incubating said analog unbound to any test compound with said chemical probing reagent and monitoring for an effect of said reagent on the unbound analog, and comparing any effects of said probing reagent on said analog in said binding complex and on said unbound analog, wherein prevention of an effect of said reagent on said analog in said binding complex caused by said reagent on said unbound analog indicates that said test compound has potential therapeutic activity.

25. An in situ footprinting assay of claim 24, wherein said chemical probing reagent is dimethyl sulfate, kethoxal, or carbodiimmide.

26. An in situ footprinting assay of claim 24, wherein said probing reagent covalently modifies a nucleotide in said artificial oligoribonucleotide analog when unbound to any test compound.

27. An in situ footprinting assay of claim 26, wherein the effect of said probing reagent is monitored by use of a labelled oligonucleotide that hybridizes to said artificial oligoribonucleotide analog when protected by said test compound from methylation, and does not hybridize to said artificial oligoribonucleotide analog when methylated by said reagent, the presence of said label after completion of said assay indicating that said test compound has potential therapeutic activity.

28. An in situ footprinting assay of claim 27, wherein said labelled oligonucleotide has the sequence CAGUGU.

29. An in situ footprinting assay of claim 26, wherein the effect of said probing reagent is monitored by use of an oligonucleotide primer that is complementary to a portion of said artificial oligoribonucleotide analog, a labelled nucleotide, and reverse transcriptase, wherein extension of said primer on said analog with said labelled nucleotide does not occur when said artificial oligoribonucleotide analog is methylated by said reagent, the presence of said label after completion of said assay indicating that said test compound has potential therapeutic activity.

30. An in situ footprinting assay of claim 29, wherein said oligonucleotide primer has the sequence TTCACCCG-GAAGGTG (SEQ ID NO:12).

31. An analog of claim 1, wherein said ligand is an aminoglycoside.

* * * * *